(12) United States Patent
Leung et al.

(10) Patent No.: US 7,510,858 B2
(45) Date of Patent: Mar. 31, 2009

(54) IRAK 1C SPLICE VARIANT AND ITS USE

(75) Inventors: Wai-Ping Leung, San Diego, CA (US); Navin Rao, San Diego, CA (US)

(73) Assignee: Janssen Pharmaceutica N.V., Beerse (BE)

(*) Notice: Subject to any disclaimer, the term of this patent is extended or adjusted under 35 U.S.C. 154(b) by 0 days.

(21) Appl. No.: 11/659,168

(22) PCT Filed: Aug. 2, 2005

(86) PCT No.: PCT/US2005/027656

§ 371 (c)(1),
(2), (4) Date: Feb. 1, 2007

(87) PCT Pub. No.: WO2006/017621

PCT Pub. Date: Feb. 16, 2006

(65) Prior Publication Data

US 2007/0243181 A1 Oct. 18, 2007

Related U.S. Application Data

(60) Provisional application No. 60/598,407, filed on Aug. 2, 2004.

(51) Int. Cl.
*C12N 15/54* (2006.01)
*C12N 9/12* (2006.01)
*C12N 15/79* (2006.01)
*C12N 15/85* (2006.01)

(52) U.S. Cl. .................... 435/194; 435/325; 435/252.3; 435/320.1; 536/23.2

(58) Field of Classification Search ........................ None
See application file for complete search history.

(56) References Cited

U.S. PATENT DOCUMENTS

| 4,366,241 | A | 12/1982 | Tom et al. |
| 4,376,110 | A | 3/1983 | David et al. |
| 4,517,288 | A | 5/1985 | Giegel et al. |
| 4,673,641 | A | 6/1987 | George et al. |
| 4,837,168 | A | 6/1989 | de Jaeger et al. |
| 4,873,316 | A | 10/1989 | Meade et al. |
| 5,010,175 | A | 4/1991 | Rutter et al. |
| 5,272,071 | A | 12/1993 | Chappel |
| 5,856,099 | A | 1/1999 | Miraglia et al. |
| 6,166,289 | A * | 12/2000 | Harris et al. .................. 800/18 |
| 6,541,623 | B1 | 4/2003 | Ford et al. |
| 2007/0031847 | A1* | 2/2007 | Cargill et al. .................. 435/6 |

FOREIGN PATENT DOCUMENTS

WO    WO 9106667    5/1991

OTHER PUBLICATIONS

Aiura et al., "Interleukin-1 Receptor Antagonist Blocks Hypotension In A Rabbit Model Of Gram Positive Septic Shock", *Cytokine*, 1991, vol. 3, p. 498.

(Continued)

*Primary Examiner*—Rebecca E Prouty
*Assistant Examiner*—William W Moore

(57) ABSTRACT

IRAK 1c [Interleukin-1 Receptor-Associated Kinase 1c] splice variants and their preparation and use are described. The splice variants may be used in drug screening assays and methods for diagnosing medical conditions mediated by IRAK 1c-modulating activity.

6 Claims, 17 Drawing Sheets

OTHER PUBLICATIONS

Akerstrom et al., "Protein G: A Powerful Tool for Binding and Detection of Monoclonal and Polyclonal Antibodies", *J Immunol.*, 1985, vol. 135(4), pp. 2589-2592.

Akira et al., "Toll-Like Receptor Signaling", *Nat Rev Immunol.*, 2004, vol. 4, pp. 499-511.

Baeuerle et al., "Function and Activation of NF-κB in the Immune System", *Annu Rev Immunol.*, 1994, vol. 12, pp. 141-179.

Banerji et al., "A Lymphocyte-Specific Cellular Enhancer is Located Downstream of the Joining Region in Immunoglobulin Heavy Chain Genes", *Cell*, 1983, vol. 33, pp. 729-740.

Beg et al., "Tumor Necrosis Factor and Interleukin-1 Lead to Phosphorylation and Loss Of IκBα: A Mechanism for NF-κB Activation", *Mol Cell Biol.*, 1993, vol. 13(6), pp. 3301-3310.

Burns et al., "Tollip, A New Component of the IL-1RI Pathway, Links IRAK to the IL-1 Receptor", *Nat Cell Biol.*, 2000, vol. 2, pp. 346-351.

Burns et al., "Inhibition of Interleukin 1 Receptor/Toll-like Receptor Signaling Through the Alternatively Spliced, Short Form of MyD88 Is Due to Its Failure to Recruit IRAK-4", *J Exp Med.*, 2003, vol. 197(2), pp. 263-268.

Byrne et al., "Multiplex Gene Regulation: A Two-Tiered Approach to Transgene Regulation in Transgenic Mice", *Proc. Natl. Acad. Sci. U.S.A.*, 1989, vol. 86, pp. 5473-5477.

Calame et al., "Transcriptional Controlling Elements in the Immunoglobulin and T Cell Receptor Loci", *Adv Immunol.*, 1988, vol. 43, pp. 235-275.

Camper et al., "Postnatal Repression of the α-Fetoprotein Gene is Enhancer Independent", *Genes Dev.*, 1989, vol. 3, pp. 537-546.

Cao et al., "TRAF6 is a Signal Transducer for Interleukin-1", *Nature*, 1996, vol. 383, pp. 443-446.

Clark-Curtiss et al., "Analysis of Recombinant DNA Using *Escherichia coli* Minicells", *Methods Enzymol.*, 1983, vol. 101, pp. 347-362.

Colley et al., "Conversion of a Golgi Apparatus Sialyltransferase to a Secretory Protein by Replacement of the NH2-Terminal Signal Anchor with a Signal Peptide", *J Biol Chem.*, 1989, vol. 264(30), pp. 17619-17622.

Collins et al., "A Common Theme In Endothelial Activation: Insights From The Structural Analysis Of The Genes For E-Selectin And VCAM-1", *Trends Cardiovasc Med.*, 1993, vol. 3(3), pp. 92-97.

Dinarello, "Interleukin-1 And Interleukin-1 Antagonism", *Blood*, 1991, vol. 77(8), pp. 1627-1652.

Dinarello et al., "The Role of Interleukin-1 in Disease", *N Engl J Med.*, 1993, vol. 328(2), pp. 106-113 and vol. 328(10), p. 744.

Dinarello, "Modalities For Reducing Interleukin 1 Activity In Disease", *Immunol Today*, 1993, vol. 14(6), pp. 260-264.

Dinarello, "The Interleukin-1 Family: 10 Years Of Discovery", *FASEB J.*, 1994, vol. 8, pp. 1314-1325.

Dunne et al., "The Interleukin-1 Receptor/Toll-Like Receptor Superfamily: Signal Transduction During Inflammation and Host Defense", *Sci STKE.*, 2003, vol. 2003(171/re3), pp. 3-17.

Edlund et al., "Cell-Specific Expression of the Rat Insulin Gene: Evidence for Role of Two Distinct 5' Flanking Elements", *Science*, 1985, vol. 230, pp. 912-916.

Fields et al., "A Novel Genetic System to Detect Protein-Protein Interactions", *Nature*, 1989, vol. 340, pp. 245-246.

Fischer et al., "Comparison Between Effects of Interleukin-1α Administration and Sublethal Endotoxemia in Primates", *Am J Physiol.*, 1991, vol. 261, pp. R442-R452.

Furka et al., "General Method for Rapid Synthesis of Multicomponent Peptide Mixtures", *Int J Peptide Protein Res.*, 1991, vol. 37, pp. 487-493.

Gingeras et al., "Simultaneous Genotyping and Species Identification Using Hybridization Pattern Recognition Analysis of Generic Mycobacterium DNA Arrays", *Genome Res.*, 1998, vol. 8, pp. 435-448.

Grilli et al., "NF-κB and Rel: Participants in a Multiform Transcriptional Regulatory System", *Int Rev Cytol.*, 1993, vol. 143, pp. 1-62.

Guice et al., "Anti-Tumor Necrosis Factor Antibody Augments Edema Formation In Caerulein-Induced Acute Pancreatitis", *J Surg Res.*, 1991, vol. 51, pp. 495-499.

Gunthard et al., "Comparative Performance of High-Density Oligonucleotide Sequencing and Dideoxynucleotide Sequencing of HIV Type 1 pol from Clinical Studies", *AIDS Res Hum Retroviruses*, 1998, vol. 14(10), pp. 869-876.

Haase et al., "Detection of Viral Nucleic Acids by in Situ Hybridization", *Methods Virol.*, 1984, vol. VII, pp. 189-226.

Hacia et al., "Two Color Hybridization Analysis Using High Denisty Oligonucleotide Arrays and Energy Transfer Dyes", *Nucleic Acids Res.*, 1998, vol. 26(16), pp. 3865-3866.

Hardy et al., "The Murine IRAK2 Gene Encodes Four Alternatively Spliced Isoforms, Two of Which Are Inhibitory", *J Biol Chem.*, 2004, vol. 279(26), pp. 27699-27708.

Heath et al., "Role of Interleukin-6 in Mediating the Acute Phase Protein Response and Potential as an Early Means of Severity Assessment in Acute Pancreatitis", *Gut*, 1993, vol. 34, pp. 41-45.

Houghten et al., "Generation and Use of Synthetic Peptide Combinatorial Libraries for Basic Research and Drug Discovery", *Nature*, 1991, vol. 354, pp. 84-86.

Janssens et al., "Regulation of Interleukin-1 and Lipopolysaccharide-Induced NF-κB Activation by Alternative Splicing of MyD88", *Curr Biol.*, 2002, vol. 12, pp. 467-471.

Janssens et al., "MyD88s, a Splice Variant of MyD88, Differentially Modulates NF-κB and AP-1-Dependent Gene Expression", *FEBS Lett.*, 2003, vol. 548, pp. 103-107.

Janssens et al., "Functional Diversity and Regulation of Different Interleukin-1 Receptor-Associated Kinase (IRAK) Family Members", *Mol Cell.*, 2003, vol. 11, pp. 293-302.

Jefferies et al., "Transactivation by the p65 Subunit of NF-κB in Response to Interleukin-1 (IL-1) Involves MyD88, IL-1 Receptor-Associated Kinase 1, TRAF-6, and Rac1", *Mol Cell Biol.*, 2001, vol. 21(14), pp. 4544-4552.

Jensen et al., "IRAK1b, A Novel Alternative Splice Variant of Interleukin-1 Receptor-Associated Kinase (IRAK), Mediates Interleukin-1 Signaling and Has Prolonged Stability", *J Biol Chem.*, 2001, vol. 276(31), pp. 29037-29044.

Jiang et al., "Interleukin-1 (IL-1) Receptor-Associated Kinase-Dependent IL-1-Induced Signaling Complexes Phosphorylate TAK1 and TAB2 at the Plasma Membrane and Activate TAK1 in the Cytosol", *Mol Cell Biol.*, 2002, vol. 22(20), pp. 7158-7167.

Kanakaraj et al., "Interleukin (IL)-1 Receptor-Associated Kinase (IRAK) Requirement for Optimal Induction of Multiple IL-1 Signaling Pathways and IL-6 Production", *J Exp Med.*, 1998, vol. 187(12), pp. 2073-2079.

Kanakaraj et al., "Defective Interleukin (IL)-18-Mediated Natural Killer and T Helper Cell Type 1 Responses in IL-1 Receptor-Associated Kinase (IRAK)-Deficient Mice", *J Exp Med.*, 1999, vol. 189(7), pp. 1129-1138.

Kaufman et al., "Translational Efficiency of Polycistronic mRNAs and Their Utilization to Express Heterologous Genes in Mammalian Cells", *EMBO J.*, 1987, vol. 6(1), pp. 187-193.

Kessel et al., "Murine Developmental Control Genes", *Science*, 1990, vol. 249, pp. 374-349.

Knop et al., "Effects of IL-1 Receptor-Associated Kinase (IRAK) Expression on IL-1 Signaling are Independent of Its Kinase Activity", *FEBS Lett.*, 1999, vol. 448, pp. 81-85.

Kobayashi et al., "IRAK-M is a Negative Regulator of Toll-Like Receptor Signaling", *Cell*, 2002, vol. 110, pp. 191-202.

Kollewe et al., "Sequential Autophosphorylation Steps in the Interleukin-1 Receptor-Associated Kinase-1 Regulate its Availability as an Adapter in Interleukin-1 Signaling", *J Biol Chem.*, 2004, vol. 279(7), pp. 5227-5236.

Kozal et al., "Extensive Polymorphisms Observed in HIV-1 Clade B Protease Gene Using High-Density Oligonucleotide Arrays", *Nat Met.*, 1996, vol. 2(7), pp. 753-759.

Krasnow et al., "Tumor Necrosis Factor-α, Interleukin 1, and Phorbol Myristate Acetate Are Independent Activators Of NF-κB Which Differentially Activate T Cells", *Cytokine*, 1991, vol. 3(5), pp. 372-379.

Kronvall, "A Surface Component in Group A, C, and G Streptococci with Non-Immune Reactivity for Immunoglobulin G", *J Immunol.*, 1973, vol. 111(5), pp. 1401-1406.

Lenardo et al., "NF-κB: A Pleiotropic Mediator of Inducible and Tissue-Specific Gene Control", *Cell*, 1989, vol. 58, pp. 227-229.

Li et al., "IL-1-Induced NF-κB and c-Jun N-Terminal Kinase (JNK) Activation Diverge at IL-1 Receptor-Associated Kinase (IRAK)", *PNAS*, 2001, vol. 98(8), pp. 4461-4465.

Li et al., "IRAK-4: A Novel Member of the IRAK Family with the Properties of an IRAK-Kinase", *PNAS*, 2002, vol. 99(8), pp. 5567-5572.

Liou et al., "Regulation Of The NF-κB/rel Transcription Factor And IκB Inhibitor System", *Curr Opin Cell Biol.*, 1993, vol. 5, pp. 477-487.

Lockhart et al., "Expression Monitoring by Hybridization to High-Density Oligonucleotide Arrays", *Nat Biotechnol.*, 1996, vol. 14, pp. 1675-1680.

Lye et al., "The Role of Interleukin 1 Receptor-Associated Kinase-4 (IRAK-4) Kinase Activity in IRAK-4-Mediated Signaling", *J Biol Chem.*, 2004, vol. 279(39), pp. 40653-40658.

Martin et al., "Summary and Comparison of the Signaling Mechanisms of the Toll/Interleukin-1 Receptor Family", *Biochim Biophys Acta*, 2002, vol. 1592, pp. 265-280.

Maschera et al., "Overexpression of an Enzymically Inactive Interleukin-1-Receptor-Associated Kinase Activates Nuclear Factor-κB", *Biochem J.*, 1999, vol. 339, pp. 227-231.

Matson et al., "Biopolymer Synthesis on Polypropylene Supports: Oligonucleotide Arrays", *Anal Biochem.*, 1995, vol. 224, pp. 110-116.

Mestas et al., "Of Mice and Not Men: Differences Between Mouse and Human Immunology", *J Immunol.*, 2004, vol. 172, pp. 2731-2738.

Morrison, "Transformation in *Escherichia coli*: Cryogenic Preservation of Competent Cells", *J Bacteriol.*, 1977, vol. 132(1), pp. 349-351.

Mosbach et al., "Formation of Proinsulin by Immobilized Bacillus Subtilis", *Nature*, 1983, vol. 302, pp. 543-545.

Ohlsson et al., "Interleukin-1 Receptor Antagonist Reduces Mortality From Endotoxin Shock", *Nature*, 1990, vol. 348, pp. 550-552.

Okusawa et al., "Interleukin 1 Induces a Shock-like State in Rabbits", *J Clin Invest.*, 1988, vol. 81, pp. 1162-1172.

Osborn et al., "Tumor Necrosis Factor α and Interleukin 1 Stimulate the Human Immunodeficiency Virus Enhancer by Activation of the Nuclear Factor κB", *PNAS U.S.A.*, 1989, vol. 86, pp. 2336-2340.

Palva et al., "Secretion of Interferon by Bacillus Subtilis", *Gene*, 1983, vol. 22, pp. 229-235.

Picard et al., "Pyogenic Bacterial Infections in Humans with IRAK-4 Deficiency", *Science*, 2003, vol. 299, pp. 2076-2079.

Pinkert et al., "An Albumin Enhancer Located 10 kb Upstream Functions Along with Its Promoter to Direct Efficient, Liver-Specific Expression in Transgenic Mice", *Genes Dev.*, 1987, vol. 1, pp. 268-276.

Queen et al., "Immunoglobin Gene Transcription is Activated by Downstream Sequence Elements", *Cell*, 1983, vol. 33, pp. 741-748.

Rao et al., "An Essential Role of Ubiquintination in Cbl-Mediated Negative Regulation of the Src-Family Kinase Fyn", *Signal Transduction*, 2002, vol. 1-2, pp. 29-39.

Rosati et al., "Identification and Characterization of Murine IRAK-2", *Biochem Biophys Res Commun.*, 2002, vol. 297, pp. 52-58.

Seed, "An LFA-3 cDNA Encodes a Phospholipid-linked Membrane Protein Homologous to its Receptor CD2", *Nature*, 1987, vol. 329, pp. 840-842.

Shirakawa et al., "In Vitro Activation and Nuclear Translocation of NF-κB Catalyzed by Cyclic AMP-Dependent Protein Kinase and Protein Kinase C", *Mol Cell Biol.*, 1989, vol. 9(6), pp. 2424-2430.

Singer et al., "Optimization of in situ Hybridization Using Isotopic and Non-Isotopic Detection Methods", *Biotechniques*, 1986, vol. 4(3), pp. 230-246.

Steer, "How and Where Does Acute Pancreatitis Begin?", *Arch Surg.*, 1992, vol. 127, pp. 1350-1353.

Suzuki et al., "Severe Impairment of Interleukin-1 and Toll-Like Receptor Signalling in Mice Lacking IRAK-4", *Nature*, 2002, vol. 416, pp. 750-754.

Takeda et al., "Toll-Like Receptors", *Annu Rev Immunol.*, 2003, vol. 21, pp. 335-376.

Vincent et al., "CDI-Dependent Dendritic Cell Instruction", *Nat Immunol.*, 2002, vol. 3(12), pp. 1163-1168.

Vogel et al., "Differential Adapter Utilization by Toll-Like Receptors Mediates TLR-Specific Patterns of Gene Expression", *Mol Interv.*, 2003, vol. 3(8), pp. 466-477.

Wakabayashi et al., "A Specific Receptor Antagonist for Interleukin 1 Prevents *Escherichia coli*-Induced Shock in Rabbits", *FASEB J.*, 1991, vol. 5, pp. 338-343.

Wesche et al., "IRAK-M is a Novel Member of the Pelle/Interleukin-1 Receptor-Associated Kinase (IRAK) Family", *J Biol Chem.*, 1999, vol. 274(27), pp. 19403-19410.

Winoto et al., "A Novel, Inducible and T Cell-Specific Enhancer Located at the 3' End of the T Cell Receptor α Locus", *EMBO J.*, 1989, vol. 8(3), pp. 729-733.

Yagasaki et al., "Exip, A Splicing Variant of p38α, Participates in Interleukin-1 Receptor Proximal Complex and Downregulates NF-κB Pathway", *FEBS Letters*, 2004, vol. 575, pp. 136-140.

Yamin et al., "The Interleukin-1 Receptor-Associated Kinase is Degraded by Proteasomes Following its Phosphorylation", *J Biol Chem.*, 1997, vol. 272(34), pp. 21540-21547.

Yanagisawa et al., "A Novel Splice Variant of Mouse Interleukin-1-Receptor-Associated Kinase-1 (IRAK-1) Activates Nuclear Factor-κB (NF- κB) and c-Jun N-Terminal Kinase (JNK)", *Biochem J.*, 2003, vol. 370, pp. 159-166.

Yeo et al., "CpG DNA Induces Self and Cross-Hyporesponsiveness of RAW264.7 Cells in Response to CpG DNA and Lipopolysaccharide: Alterations in IL-1 Receptor-Associated Kinase Expression", *J Immunol.*, 2003, vol. 170, pp. 1052-1061.

* cited by examiner

Fig. 2A

SEQ ID NO: 1:  5' GAC CAA GTA TCT GAA AGA CCT GGT G 3'

SEQ ID NO: 2:  5' GAC CAA GTA TCT GGT GTA CGA GAG 3'

SEQ ID NO: 3:  5' TCA GCT CTG AAA TTC ATC ACT TTC 3'

SEQ ID NO: 4  5' ACG GTG TAT GCT GTG GCG AGG CTG AAG GAG AAC 3'

SEQ ID NO: 5  5' TGC CAC ATA CGA CAC CGC TCC GAC TTC CTC TTG 3'

Fig. 2B

SEQ ID NO: 6

5' ATGGCCGGGGGCCGGGGCCGGGGAGCCCGCAGCCCCCGGCGCCCCAGCACTTCTTGTACGAGGTGCCGCCCTG
GGTCATGTGCCGGCTTCTACAAAGTGATGGACGCCCTGGAGCCCGACTGGTGCCAGTTCGCCGCCCTGATCGTG
CGCGACCAGAGCCGAGCTGCGCGTTCGCGGGCACGGCCAGCAGCAGCGCGCTCCGGCACCTGGCGAGCGCCCGAGTTCCTGCCCTGTGCCGGATCAAC
CGCAAGCCCGAGCTGTGCCGCGACCCGTTCCGTGCACCTGTCCGTGCCCAGCGTGTCCGTGCGGGACATCATCACAG
CCTGGCACCCTCCCGCGTTCCGTCCGAGCACCACTGCCCCGAGGCCAGCATCCTCCCCAGCATCCTGCACCGCCG
AGGCCGAGCCCTGGAGCCCCGGAAGTTGCCATCCTCCAGCCCTTTCCAGGCTCCCA
GACCCATTCAGGGCCTGAGCTGCGCTGGTTCCAAGCCCTGTGCCCTCCACCGCCATCTCCAGCCCT
TCTTCTACCAAGCCAGCCCAGAGAGCTCAGTGTCCCTCCTGCAGGAGCCCCTCTCCGTTTGCTGCCCC
TCTGTGAGATTTCCCGGGGCACCCACACAACTTCTCGGAGAGCTCAAGATGCGGGAGGTGGCTTTGGGTGCGTGTA
CCGGGCGGTGATGAGGAACACGGTTATGCTGTGAAGAGGCTGAAGGAGAACGCTGACCTGGAGTGGACTGCAGTG
AAGCAGAGCTTCCTGACCGAGCTGTCCAGGTTTCGTCCCCAAACATTGTGGACTTTGCTGCTACTG
TGCTCAGAACGGCTTCTACTGCCTGGTTGCCTGTACGGCTTCCTGGAGGACCCGTCTCCACTGCCAG
ACCCAGGCCTGCCCACCTCTCCTGGCCATCCATGGAGACATCAAGAGTTCCAACGTCCTTCTGATGAGAGGCTGACACCCA
ACATCAGGACACAGCCCCAGCCTCATCCATGGAGAGACATCAAGACGTCCTTCTGGATGAGAGGCTGACACCCA
AGCTGGGAGACTTTGGCCTGCGGGACACCCTGGCCCCGGAGAGTACATCAAGACGGGAAGGCTGGCTGTGGACA
GGACACAGACAGTGCGCCACCTGACCTGAGCTTTGGGGTGTAGTGCTAGAAGGAGGGCTGGAAGGAGGCTGTCCCATGCCCAGCTGGGCCCCAGCTGGCCCCAGCTGGAGACGGCACGGTGCCAG
CGGAACACCTTCAGCTTTGGGGTGTAGTGCTAGAAGGAGGGCTGGGTGCTGTCCCATGCCCAGCTGGGCCCAGCTGGA
GACCAAGTATCTGAAAGACTGGCTGCAGATGCCTGGGCTGTGCCCATGCCCAGCTGGGCCCAGCAGCTGGAAGAACGGGGTGAAGACGGCACGGTGCCAG
CTGCAAGCAGGTCTGGCTGCCCCACCTGACCTATGACCAGGTCTAGAGAAGAAGAAGTGGCTGCTGCTGCCAAGAAGCACCTGCACCGGCC
GCCCCGGCCCTGGCTGCACCTGCGGGCTGTACGAGCAGTGGTGGGGGGTGCCCGGG
AAAAGGAGGGCCTCTAGACGGAGCTAGAGAAGAAGCAGTGCAGAGAACTCCTACGTGTCCAGCACTGGCAGAGCCACA
CATTTGGAGGCGCCGCTGCCATGGAGCCCCTGCAGCCCCATCAGGAGCCAGTGCCCAGCCAGTGCAGAGAG
GCCCCAACGCTGCCTCTGAGAGCCCGTGTCCCAGGGGACACCCCTGGAAGCCTCCTGCCCTCTGCCACTTGACTCC
AGCTGCCCCTCTGACCAACCAGCAGCCCCCCAGGGGGACAACGGCAGGAGAATCGAGCTG
GGGGAGTGCCAGGATCCCGGCCCACAGCCCGGCCGTGAAGAAGATGTTGGCAGCTCTGCATCATCGTCATCAGA
GCCACCGCAGATTATCATCAACCCTGCCCGACAGAGAAGATGTTCCAGAAGCTGGCCCTGTACGAGGATGGGCCCTG
GACAGCCTGCAGCTGCTGTCGTCCCCTCCCCAGCTCGTGTGCTTGGGCCTTGGAACAGGACAGGAGGAGGGGCCCGAAGAA
AGTGATGAATTTCAGAGCTGA 3'

Fig. 2C

SEQ ID NO: 7

5' ATGGCCGGGGGCCGGGGCCGGGGAGCCAGCCCCCGGGCCGCCCTGCCGCCCTG
GGTCATGTGCCGCTTCTACAAAGTGATGGACGCCCTGGAGCCCGCCAGTTCGCCGCCCTGATCGTG
CGCGACCAGACCGAGCTGCGGCTGCGTGCGCAGGCCACGGCCAGCGTCCTGTGGCCCTGGATCAAC
CGCAACGCCCGTGTGCTGGCCGACCTCGTGTGCACATCCTCACGCACTGAGCTGCTCCGTGCGGATCATCACAG
CCTGGCACCCTCCCGCCCGCTTCCGTCCCAGCAACACTGCCCCAGCACATCCCTGCACCCGCCG
AGGCCGAGGCCTGGAGCCCCGGAAGTTGCCATCCTCAGCCTTCCTCTCCCAGCTTTCCAGGCTCCCAG
ACCCATTCAGGGCCTGAGCTCGGCCTGGTTCCAAGCCCTGCTTCCCTGTGCCTCCAGCCCCTTC
TTCTACCAAGCCAGCCCGGGGCACCCACAACTTCTCGGAGAGCTCAAGATCGGGGGAGGTGGCTTTGGGTGCGTGTACCG
GTGAGATTTCCCGGGGGCACCCACAACTTCTCGGAGAGCTCAAGATCGGGGGAGGTGGCTTTGGGTGCGTGTACCG
GGCGGTGATGAGGAACACGGTGTATGCTGTGAAGAGGCTGAACGCTGACCTGGAGTGACTGCAGTGAAG
CAGAGCTTCCTGACGGAGGTGGAGCAGCTGTGTACGGCCTGTCCAGGTTTCGTCACCCAAACATTGTCTGCTACTGTGC
TCAGAACGGCTTCTACTGCCTGCCTCAGCGACTGGACATCCTTCTGGGTACAGCCCGGGGCAATTCAGTTTCTACAT
AGGCCTGCCACCTCTCTCCTGGCCTCAGCGACTGGACATCCTTCTGGGTACAGCCCGGGGCAATTCAGTTTCTACAT
CAGGACAGCCCCAGCCTCATCCATGGAGACATCAAGAGTTCCAACGTCCTTCTGGATGAGAGGCTGACACCCAAGCT
GGGAGACTTTGGCCCGGTTCAGCGTCCCCGGTTCAGCGACCTTGGCTGTAGTGCTAGAGAAGCTGCAGGCAGTGGTGCTGTGGACACGGAC
ACAGAACAGTGCGGGGGCACCCTGGAGCCACCCTGGCTGTAGTGCTAGAGAAGCTGCAGGCAGTGGTGCTGTGGACACGGAC
ACCTTCAGCTTTGGGGTGGTAGTGCTAGAGAAGCTAGAGAAGCTGAAGACGCACGGTGCCAGGACCA
AGTATCTGGTGTACGAGAGGATGGCAGGAAGAAGCTAGAGAAGCTGAAGACGCACGGTGCCAGGACCA
GCTGCATCCCCCTTCCCCGGCATCAGGAGCCAGTCGAGCCACTGGCAGAGCCAGAGCTGCAACCAGCCCGT
GCAGCCCCTGACGAGAGCCAGCGTGGCAGAGCCAGAGCTGCAACCAGCCCGT
GGAGAGTGACAGAGAGCTAGGCGGCCGCCTCTCTGCTGCCGGCCTTGACTCCAAGCTGCCCTCTGAC
CCAGCACCCCTGTGTCCTCAGGGAGGCCGGCAGGAGAATCGAGCTGGGGAGTGGCCAGGA
TCCCGGCCCCACACTGGCCCTTGGCAGCTCTGCATCATCGTCGAGAGCCACCGGAGATTATCAT
CAACCCTGCCCAGCCCTGCCAGAAGATGGTCCAGAGCTCCAGAGCCAGCCACCGGAGATTATCAT
TCGTCCAGCTCCCTGCCCAGCCCTGCCAGAAGATGGTCCAGAGCTCCAGAGCCCTGGACACCGAGAGAGCCACCGGAGATTATCAT
GA 3'

Fig. 2D

SEQ ID NO: 8

5' AAAGACCTGGTGGAAGAGGAGGCTGAGGAGGCTGAGTGGCTTTGAGAAGCACCCAGAGCACACTGCAAGCAGGT CTGGCTGCAGATGCCTGGGCTGCTCCCATGCCATGCAGATCTACAAGAAGCACCTGGACCCCAGGCCCGGGCCC TGCCCACCTGAGCTGGGCCTGGCCTGGCCTGGCCCAGCTGCCTGCTGCCTGCACCGCCGGGGCCAAAAGGAGGCC TCCTATGACCCAG 3'

Fig. 2E

SEQ ID NO: 9

MAGGPGPGEPVVPGAQHFLYEVPPWVMCRFYKVMDALEPADWCQFAALIVRDQTELRLCERSEQRTASVLWPWINRNA RVADLVHILTHLQLLRARDIITAWHPPAPVVPPSTAAPRPSSISAGSEAGDWSPRKLQSSASTFLSPAFPGSQTHSESELLQ VPLPVSLGPPLPSSAPSSTKSSPESPVSGLQRAHPSPFCWPFCEISQGTCNFSEELRIGEGGFGCVYRAVMRNTTYAVKRL KEEADLEWTMVKQSFLTEVEQLSRFRHPNIVDFAGYCAESGLYCLVYGFLPNGSLEDQLHLQTQACSPLSWPQRLDILLGT ARAIQFLHQDSPSLIHGDIKSSNVLLDERLMPKLGDFGLARFSRFAGAKASQSSTVARTSTVRGTLAYLPEEYIKTGRLAVDT DTFSFGVVILETLAGQRAVRTQGAKTKYLKDLIEDEAEEAGVTLKSTQPTLWVGVATDAWAAPIAAQIYKKHLDSRPGPCPP QLGLALAQLACCCMHRRAKKRPPMTQVPTQAQRPSERLAVPREALPENQV

SEQUENCE LISTING

<160> NUMBER OF SEQ ID NOS: 9

<210> SEQ ID NO 1
<211> LENGTH: 25
<212> TYPE: DNA
<213> ORGANISM: Artificial
<220> FEATURE:
<223> OTHER INFORMATION: IRAK1 forward primer

<400> SEQUENCE: 1
gaccaagtat ctgaaagacc tggtg                                          25

<210> SEQ ID NO 2
<211> LENGTH: 24
<212> TYPE: DNA
<213> ORGANISM: Artificial
<220> FEATURE:
<223> OTHER INFORMATION: IRAK1c forward primer

<400> SEQUENCE: 2
gaccaagtat ctggtgtacg agag                                           24

<210> SEQ ID NO 3
<211> LENGTH: 24
<212> TYPE: DNA
<213> ORGANISM: Artificial
<220> FEATURE:
<223> OTHER INFORMATION: IRAK1/IRAK1c reverse primer

<400> SEQUENCE: 3
tcagctctga aattcatcac tttc                                           24

<210> SEQ ID NO 4
<211> LENGTH: 33
<212> TYPE: DNA
<213> ORGANISM: Artificial
<220> FEATURE:
<223> OTHER INFORMATION: IRAK1 K239A kinase-dead forward primer

<400> SEQUENCE: 4
acggtgtatg ctgtggcgag gctgaaggag aac                                 33

<210> SEQ ID NO 5
<211> LENGTH: 33
<212> TYPE: DNA

<213> ORGANISM: Artificial
<220> FEATURE:
<223> OTHER INFORMATION: IRAK1 K239A kinase-dead reverse primer

<400> SEQUENCE: 5
tgccacatac gacaccgctc cgacttcctc ttg        33

<210> SEQ ID NO 6
<211> LENGTH: 2139
<212> TYPE: DNA
<213> ORGANISM: Artificial
<220> FEATURE:
<223> OTHER INFORMATION: human IRAK1 full length cDNA

<400> SEQUENCE: 6

| | | | | | |
|---|---|---|---|---|---|
| atggccgggg | ggccgggccc | ggggagccc | gcagccccg | gcgcccagca | cttcttgtac | 60 |
| gaggtgccgc | cctgggtcat | gtgccgcttc | tacaaagtga | tggacgccct | ggagcccgcc | 120 |
| gactggtgcc | agttcgccgc | cctgatcgtg | cgcgaccaga | ccgagctgcg | gctgtgcgag | 180 |
| cgctccgggc | agcgcacggc | cagcgtcctg | tggccctgga | tcaaccgcaa | cgcccgtgtg | 240 |
| gccgacctcg | tgcacatcct | cacgcacctg | cagctgctcc | gtgcgcggga | catcatcaca | 300 |
| gcctggcacc | ctcccgcccc | gcttccgtcc | ccaggcacca | ctgccccgag | gcccagcagc | 360 |
| atccctgcac | ccgccgaggc | cgaggcctgg | agccccgga | agttgccatc | tcagcctcc | 420 |
| accttcctct | ccccagcttt | tccaggctcc | cagacccatt | cagggcctga | gctcggcctg | 480 |
| gttccaagcc | ctgcttccct | gtggcctcca | ccgccatctc | cagccccttc | ttctaccaag | 540 |
| ccaggcccag | agagctcagt | gtccctcctg | cagggagccc | gcccctctcc | gttttgctgg | 600 |
| cccctctgtg | agatttcccg | ggcacccac | aacttctcgg | aggagctcaa | gatcggggag | 660 |
| ggtggctttg | ggtgcgtgta | ccgggcggtg | atgaggaaca | cggtgtatgc | tgtgaagagg | 720 |
| ctgaaggaga | cgctgaccct | ggagtggact | gcagtgaagc | agagcttcct | gaccgaggtg | 780 |
| gagcagctgt | ccaggtttcg | tcacccaaac | attgtggact | tgctggctac | tgtgctcag | 840 |
| aacggcttct | actgcctggt | gtacggcttc | ctgcccaacg | gctccctgga | ggaccgtctc | 900 |
| cactgccaga | cccaggcctg | cccacctctc | tcctggcctc | agcgactgga | catccttctg | 960 |
| ggtacagccc | gggcaattca | gtttctacat | caggacagcc | ccagcctcat | ccatggagac | 1020 |
| atcaagagtt | ccaacgtcct | tctggatgag | aggctgacac | ccaagctggg | agactttggc | 1080 |
| ctggcccggt | tcagccgctt | tgccgggtcc | agcccagcc | agagcagcat | ggtggcccgg | 1140 |
| acacagacag | tgcggggcac | cctggcctac | ctgcccgagg | agtacatcaa | gacgggaagg | 1200 |
| ctggctgtgg | acacggacac | cttcagcttt | ggggtggtag | tgctagagac | cttggctggt | 1260 |
| cagagggctg | tgaagacgca | cggtgccagg | accaagtatc | tgaaagacct | ggtggaagag | 1320 |
| gaggctgagg | aggctggagt | ggcttttgaga | agcacccaga | gcacactgca | agcaggtctg | 1380 |
| gctgcagatg | cctgggctgc | tcccatcgcc | atgcagatct | acaagaagca | cctggacccc | 1440 |
| aggcccgggc | cctgcccacc | tgagctgggc | ctgggcctgg | gccagctggc | ctgctgctgc | 1500 |
| ctgcaccgcc | gggccaaaag | gaggcctcct | atgacccagt | gtacgagag | ctagagaag | 1560 |
| ctgcaggcag | tggtggcggg | ggtgcccggg | catttggagg | ccgccagctg | catcccccct | 1620 |
| tccccgcagg | agaactccta | cgtgtccagc | actggcagag | cccacagtgg | ggctgctcca | 1680 |
| tggcagcccc | tggcagcgcc | atcaggagcc | agtgcccagg | cagcagagca | gctgcagaga | 1740 |
| ggccccaacc | agcccgtgga | gagtgacgag | agcctaggcg | gcctctctgc | tgccctgcgc | 1800 |
| tcctggcact | tgactccaag | ctgccctctg | gacccagcac | cctcaggga | ggccggctgt | 1860 |

```
cctcagggqq acacqqcaqq aqaatcqaqc tqqqqqaqtq qcccaqqatc ccqqcccaca    1920 gccgtggaag gactggccct tggcagctct gcatcatcgt cgtcagagcc accgcagatt    1980
atcatcaacc ctgcccgaca gaagatggtc cagaagctgg ccctgtacga ggatggggcc    2040
ctggacagcc tgcagctgct gtcgtccagc tccctcccag gcttgggcct ggaacaggac    2100
aggcaggggc cgaagaaag tgatgaattt cagagctga                            2139

<210> SEQ ID NO 7
<211> LENGTH: 1902
<212> TYPE: DNA
<213> ORGANISM: Artificial
<220> FEATURE:
<223> OTHER INFORMATION: human IRAK1c cDNA

<400> SEQUENCE: 7
atggccgggg ggccgggccc ggggagccc gcagcccccg cgcccagca cttcttgtac       60 gaggtgccgc cctgggtcat gtgccgcttc tacaaagtga tggacgccct ggagcccgcc    120
gactggtgcc agttcgccgc cctgatcgtg cgcgaccaga ccgagctgcg gctgtgcgag    180
cgctccgggc agcgcacggc cagcgtcctg tggccctgga tcaaccgcaa cgcccgtgtg    240
gccgacctcg tgcacatcct cacgcacctg cagctgctcc gtgcgcggga catcatcaca    300
gcctggcacc ctcccgcccc gcttccgtcc ccaggcacca ctgccccgag gcccagcagc    360
atccctgcac ccgccgaggc cgaggcctgg agccccgga agttgccatc ctcagcctcc    420
accttcctct ccccagcttt tccaggctcc cagacccatt cagggcctga gctcggcctg    480
gttccaagcc ctgcttccct gtggcctcca ccgccatctc cagccccttc ttctaccaag    540
ccaggcccag agagctcagt gtccctcctg cagggagccc gccctctcc gttttgctgg    600 cccctctgtg agatttcccg ggcacccac aacttctcgg aggagctcaa gatcggggag    660
ggtggctttg gtgcgtgta ccgggcgtg atgaggaaca cggtgtatgc tgtgaagagg    720
ctgaaggaga cgctgacct ggagtggact gcagtgaagc agagcttcct gaccgaggtg    780
gagcagctgt ccaggtttcg tcacccaaac attgtggact tgctggcta ctgtgctcag    840 aacggcttct actgcctggt gtacggcttc ctgcccaacg gctccctgga ggaccgtctc    900
cactgccaga cccaggcctg cccacctctc tcctggcctc agcgactgga catcttctg    960 ggtacagccc gggcaattca gtttctacat caggacagcc ccagcctcat ccatggagac   1020
atcaagagtt ccaacgtcct tctggatgag aggctgacac ccaagctggg agactttggc   1080 ctggcccgt tcagccgctt tgccgggtcc agccccagcc agagcagcat ggtggcccgg   1140
acacagacag tgcgggcac cctggcctac ctgcccgagg agtacatcaa gacgggaagg   1200
ctggctgtgg acacggacac cttcagcttt gggtggtag tgctagagac cttggctggt   1260
cagagggctg tgaagacgca cggtgccagg accaagtatc tggtgtacga gaggctagag   1320
aagctgcagg cagtggtggc gggggtgccc gggcatttgg aggccgccag ctgcatcccc   1380
ccttccccgc aggagaactc ctacgtgtcc agcactggca gagcccacag tggggctgct   1440
ccatggcagc ccctggcagc gccatcagga gccagtgccc aggcagcaga gcagctgcag   1500
agaggcccca accagcccgt ggagagtgac gagagcctag cggcctctc tgctgccctg   1560 cgctcctggc acttgactcc aagctgccct ctggacccag cacccctcag ggaggccggc   1620
tgtcctcagg gggacacggc aggagaatcg agctgggga gtgcccagg atccggccc   1680 acagccgtgg aaggactggc ccttggcagc tctgcatcat cgtcgtcaga gccaccgcag   1740
```

-continued

```
attatcatca accctgcccg acagaagatg gtccagaagc tggccctgta cgaggatggg    1800
gccctggaca gcctgcagct gctgtcgtcc agctccctcc caggcttggg cctggaacag    1860
gacaggcagg ggcccgaaga aagtgatgaa tttcagagct ga                       1902
```

<210> SEQ ID NO 8
<211> LENGTH: 237
<212> TYPE: DNA
<213> ORGANISM: Homo sapiens

<400> SEQUENCE: 8

```
aaagacctgg tggaagagga ggctgaggag gctggagtgg ctttgagaag cacccagagc     60
acactgcaag caggtctggc tgcagatgcc tgggctgctc ccatcgccat gcagatctac    120
aagaagcacc tggaccccag gcccgggccc tgcccacctg agctgggcct gggcctgggc    180
cagctggcct gctgctgcct gcaccgccgg gccaaaagga ggcctcctat gacccag       237
```

<210> SEQ ID NO 9
<211> LENGTH: 537
<212> TYPE: PRT
<213> ORGANISM: Homo sapiens

<400> SEQUENCE: 9

```
Met Ala Gly Gly Pro Gly Pro Gly Glu Pro Val Val Pro Gly Ala Gln
1               5                   10                  15

His Phe Leu Tyr Glu Val Pro Pro Trp Val Met Cys Arg Phe Tyr Lys
                20                  25                  30

Val Met Asp Ala Leu Glu Pro Ala Asp Trp Cys Gln Phe Ala Ala Leu
            35                  40                  45

Ile Val Arg Asp Gln Thr Glu Leu Arg Leu Cys Glu Arg Ser Glu Gln
        50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Pro Ala Pro Val Val Pro Pro Ser
            100                 105                 110

Thr Ala Ala Pro Arg Pro Ser Ser Ile Ser Ala Gly Ser Glu Ala Gly
        115                 120                 125

Asp Trp Ser Pro Arg Lys Leu Gln Ser Ser Ala Ser Thr Phe Leu Ser
    130                 135                 140

Pro Ala Phe Pro Gly Ser Gln Thr His Ser Glu Ser Glu Leu Leu Gln
145                 150                 155                 160

Val Pro Leu Pro Val Ser Leu Gly Pro Leu Pro Ser Ser Ala Pro
                165                 170                 175

Ser Ser Thr Lys Ser Ser Pro Glu Ser Pro Val Ser Gly Leu Gln Arg
            180                 185                 190

Ala His Pro Ser Pro Phe Cys Trp Pro Phe Cys Glu Ile Ser Gln Gly
        195                 200                 205

Thr Cys Asn Phe Ser Glu Glu Leu Arg Ile Gly Glu Gly Gly Phe Gly
    210                 215                 220

Cys Val Tyr Arg Ala Val Met Arg Asn Thr Thr Tyr Ala Val Lys Arg
225                 230                 235                 240

Leu Lys Glu Glu Ala Asp Leu Glu Trp Thr Met Val Lys Gln Ser Phe
                245                 250                 255

Leu Thr Glu Val Glu Gln Leu Ser Arg Phe Arg His Pro Asn Ile Val
```

-continued

```
                260                 265                 270
Asp Phe Ala Gly Tyr Cys Ala Glu Ser Gly Leu Tyr Cys Leu Val Tyr
            275                 280                 285
Gly Phe Leu Pro Asn Gly Ser Leu Glu Asp Gln Leu His Leu Gln Thr
            290                 295                 300
Gln Ala Cys Ser Pro Leu Ser Trp Pro Gln Arg Leu Asp Ile Leu Leu
305                 310                 315                 320
Gly Thr Ala Arg Ala Ile Gln Phe Leu His Gln Asp Ser Pro Ser Leu
                325                 330                 335
Ile His Gly Asp Ile Lys Ser Ser Asn Val Leu Leu Asp Glu Arg Leu
                340                 345                 350
Met Pro Lys Leu Gly Asp Phe Gly Leu Ala Arg Phe Ser Arg Phe Ala
            355                 360                 365
Gly Ala Lys Ala Ser Gln Ser Ser Thr Val Ala Arg Thr Ser Thr Val
            370                 375                 380
Arg Gly Thr Leu Ala Tyr Leu Pro Glu Glu Tyr Ile Lys Thr Gly Arg
385                 390                 395                 400
Leu Ala Val Asp Thr Asp Thr Phe Ser Phe Gly Val Val Ile Leu Glu
                405                 410                 415
Thr Leu Ala Gly Gln Arg Ala Val Arg Thr Gln Gly Ala Lys Thr Lys
            420                 425                 430
Tyr Leu Lys Asp Leu Ile Glu Asp Glu Ala Glu Glu Ala Gly Val Thr
            435                 440                 445
Leu Lys Ser Thr Gln Pro Thr Leu Trp Val Gly Val Ala Thr Asp Ala
            450                 455                 460
Trp Ala Ala Pro Ile Ala Ala Gln Ile Tyr Lys Lys His Leu Asp Ser
465                 470                 475                 480
Arg Pro Gly Pro Cys Pro Pro Gln Leu Gly Leu Ala Leu Ala Gln Leu
                485                 490                 495
Ala Cys Cys Cys Met His Arg Arg Ala Lys Lys Arg Pro Pro Met Thr
                500                 505                 510
Gln Val Pro Thr Gln Ala Gln Arg Pro Ser Glu Arg Leu Ala Val Pro
            515                 520                 525
Arg Glu Ala Leu Pro Glu Asn Gln Val
530                 535
```

IRAK 1C SPLICE VARIANT AND ITS USE

CROSS-REFERENCE TO RELATED APPLICATION

This is a national-phase of International Application No. PCT/US2005/027656, which bases priority, on U.S. Provisional Application No. 60/598,407, filed Aug. 2, 2004.

FIELD OF THE INVENTION

The invention generally relates to splice variants of the interleukin-1 receptor associated kinase-1 (IRAK1) that function as a natural dominant negative, which is designated herein as "IRAK1c". The invention also relates to the therapeutic use of IRAK1c splice variants in treating diseases and medical conditions.

BACKGROUND OF THE INVENTION

In mammals, challenge by bacteria and viral pathogens results in a rapid activation of the immune system to mount an expeditious, appropriate, and adequate response. The activation of specialized receptors for pathogen-associated structures on sentinel cells is translated into the production and release of endogenous alarm mediators, termed cytokines (Martin et al., 2002, *Biochemica et Biophysica Acta*, 1592(3): 265-280). The master cytokines interleukin-1 (IL-1) and tumor necrosis factor (TNF), as well as IL-12 and IL-18, are rapidly released by these cells of first line defense. For instance, they orchestrate the acute response required to support the local phagocytes in their effort to control pathogens before they can spread systemically.

During inflammation, which results from tissue injury, infection, or autoimmune diseases, such as rheumatoid arthritis (RA), cells release these inflammatory mediators eliciting the symptoms of inflammation (see Dunne et al., 2003, *Science: Signal Transduction Knowledge Environment*, 2003 (171):re3). These symptoms include vascular changes, such as increased blood flow, and extravasation and activation of leukocytes. During chronic inflammation, tissue remodeling and the production of acute-phase proteins by the liver occur. Cytokines are the key orchestrators of these processes, and the cytokine interleukin-1 (IL-1) plays a central role. Upon binding its receptor on the cell surface, IL-1 stimulates the expression of a large number of proinflammatory proteins. These include enzymes, such as inducible cyclooxygenase (which leads to the production of prostaglandins, themselves important inflammatory mediators), adhesion molecules, chemokines, tissue-degrading enzymes, and acute-phase proteins, such as serum amyloid A. The molecular basis for these effects has been studied in great detail, and many of the components in the signaling pathways that culminate in changes in gene expression have been delineated.

The importance of interleukin-1 in inflammation has been demonstrated by the ability of the highly specific interleukin-1 receptor antagonist protein to relieve inflammatory conditions (for review, see Dinarello (1991), *Blood* 77: 1627-1652; Dinarello et al. (1993), *New England J. Med.* 328:106-113; Dinarello (1994), *FASEB J.* 8:1314-1325; Dinarello (1993), *Immunol. Today* 14:260-264). Many of the proinflammatory effects of interleukin-1, such as the upregulation of cell adhesion molecules on vascular endothelia, are exerted at the level of transcriptional regulation. The transcriptional activation by interleukin-1 of cell adhesion molecules and other genes involved in the inflammatory response appears to be mediated largely by NF-kappa B (Shirakawa et al. (1989), *Mol. Cell Biol.* 9:2424-2430; Osborn et al. (1989), *Proc. Natl. Acad. Sci. USA* 86:2336-2340; Krasnow et al. (1991), *Cytokine* 3:372-379; Collins et al. (1993), *Trends Cardiovasc. Med.* 3:92-97). In response to interleukin-1, the NF-kappa B inhibitory factor I kappa B is degraded and NF-kappa B is released from its inactive cytoplasmic state to localize within the nucleus where it binds DNA and activates transcription (Liou et al. (1993), *Curr. Opin. Cell Biol.* 5:477-487; Beg et al. (1993), *Mol. Cell. Bio.* 13:3301-3310).

The ability of IL-1 to modify biological responses has been demonstrated in a variety of studies. For example, the administration of interleukin-1 to rabbits (Wakabayashi et al., *FASEB J* (1991), 5:338; Okusawa et al., *J Clin Invest* (1988), 81:1162; Ohlsson et al., *Nature* (1990), 348:550; Aiura et al., *Cytokine*, 1991, 4:498) and primates (Fischer et al., *Am J Physiol*, 1991, 261:R442) has been shown to result in hypotension, tachycardia, lung edema, renal failure, and, eventually, death, depending on the dose. When the serum from the interleukin-1 treated animals is examined, the elevation of other cytokines is evident, mimicking the levels seen in acute pancreatitis in humans. (Guice et al., *J Surg Res*, 1991, 51:495-499; Heath et al., *Pancreas*, 1993, 66:41-45). There is a body of evidence currently available which supports the role of interleukin-1 as a mediator of the systemic response to diseases such as sepsis and pancreatitis and as an activator of the remaining members of the cytokine cascade (see, e.g., Dinarello et al., *Arch Surg*, 1992, 127:1350-1353).

The TIR family appears to utilize similar signaling mechanisms to activate downstream effector mechanisms. While some components of the downstream signaling machinery, like the adapter TNF receptor associated factor 6 (TRAF6), are shared by other receptors of proinflammatory cytokines, one signaling module is exclusively employed by the TIR family. This consists of myeloid differentiation protein 88 (MyD88), interleukin-1 receptor associated kinase (IRAK) family members, and Toll interacting protein (Tollip).

Upon ligand binding, TIR family members form multimeric receptor complexes and via the cytoplasmic TIR domains recruit adaptor proteins such as MyD88, TIRAP and TRIF (Vogel et al., 2003, *Molecular Interventions* 3:466-477. This results in the sequential activation of a conserved signaling module that includes the interleukin-1 receptor associated kinases (IRAKs) and TRAF6 and activation of nuclear factor-κB (NF-κB), p38 and c-Jun N-terminal kinase (JNK) resulting in gene transcription and induction of an inflammatory response (Akira et al., 2004, *Nature Reviews Immunology*, 4:499-511).

Upon activation of TIR family members by ligand, IRAK4 and IRAK1 are recruited to the receptor complex. At the receptor, IRAK1 associates with the adaptors Tollip and MyD88. IRAK4 then activates IRAK1, resulting in IRAK1 autophosphorylation (Li et al., 2002, *Proceedings of the National Academy of Sciences USA*, 99:5567-5572; Jiang et al., 2002, *Molecular and Cellular Biology* 22:7158-7167). IRAK1 hyperphosphorylation results in termination of a complex with Tollip, disassociation from the receptor-MyD88 complex and formation of a protein complex of hyperphosphorylated IRAK1 and TRAF-6, a prerequisite for TRAF-6-mediated NF-κB activation and induction of an inflammatory response (Kollewe et al., 2004, *Journal of Biological Chemistry*, 279:5227-5236).

The IRAK family of serine-threonine kinases has four members: IRAK1, IRAK2, IRAKM and IRAK4 (Akira et al., 2004, *Nature Reviews Immunology*, 4:499-511; Janssens et al., 2003, *Molecular Cell*, 11:293-302). Despite significant structural homology between family members, they also have distinct functions. While IRAKM has been shown to function as an induced-negative regulator of TIR signaling in some contexts (Kobayashi et al., 2002, *Cell,* 110:191-202), other lines of evidence support a role for IRAKM as an activator of TIR-mediated signal transduction events (Wesche et al., 1999, *Journal of Biological Chemistry,* 274:19403-19410), leaving open the question as to the bona fide biological role played by this member of the IRAK family. IRAK2, which like IRAKM lacks kinase activity, appears to be partially redundant for IRAK1 (Kobayashi et al., 2002, *Cell* 110:191-202). Both IRAK1 and IRAK4 exhibit kinase activity. Both human and mouse IRAK4-deficiency results in non-responsiveness to a broad panel of TIR family ligands (Picard et al., 2003, *Science* 299:2076-2079; Suzuki et al., 2002, *Nature,* 416:750-756). IRAK1 deficiency results in a partial defect in TIR activation, with substantial decreases in IL-1, IL-18 and LPS responsiveness (Kanakaraj et al., 1998, *Journal of Experimental Medicine* 187:2073-2079; Kanakaraj et al., 1998, *Journal of Experimental Medicine* 189:1129-1138).

Due to the need for careful regulation of pro-inflammatory TIR signal transduction, multiple mechanisms exist to prevent tissue damage that arises from sustained inflammation. Given the key role that IRAK1 plays in induction of the inflammatory response, several mechanisms exist to regulate IRAK1. IRAK1 hyper-autophosphorylation results not only in full activation of kinase activity, but also in a decrease in protein stability, providing a purported mechanism by which to regulate IRAK1 activity (Yamin et al., 1997, *Journal of Biological Chemistry* 272:21540-21547).

Alternative splicing is another mechanism by which a single gene can generate multiple, functionally distinct protein products. A splice variant of a key adaptor protein in the TIR pathway, MyD88, can regulate signaling by serving as a dominant negative (Janssens et al., 2003, *FEBS Letters,* 548:103-107). Furthermore, several IRAK1 splice variants have been described in both human and mouse species. IRAK1b, which lacks 90 bp, arises from the use of an alternative 5'-acceptor splice site in exon 12. IRAK1b lacks kinase activity, but nonetheless facilitates TIR-mediated signaling, and exhibits a prolonged half-life (Jensen et al., 2001, *Journal of Biological Chemistry* 276:29037-29044). IRAK1s, a splice variant in mouse, is generated by a splice acceptor site in exon 12, resulting in a frame shift and generation of a premature stop codon (Yanagisawa et al., 2003, *Biochemical Journal,* 370:159-166). Although IRAK1s is kinase dead, it constitutively activates the NFκB and JNK pathway.

Therefore, there exists a need to identify and characterize a biologically active molecular target that functions as a dominant negative modulator of TIR signal transduction events. Furthermore, it would be advantageous to identify such a target that would be broadly applicable to the attenuation of signaling events governed by a wide range of TIR and TLR family members. Such an identified target amenable to exploitation would be useful in developing therapies directed against the many medical conditions, disorders, and diseases associated with aberrant TIR signaling activity. Furthermore, it would be beneficial to identify such a target, the expression of which can serve as a biomarker for certain of the pathologies and disorders associated with aberrant TIR signaling.

SUMMARY OF THE INVENTION

In one general aspect, the invention is directed to an isolated polynucleotide that encodes for a biologically active dominant negative IRAK1 alternative splice variant. A preferred embodiment of such a polynucleotide corresponds to IRAK1 with exon 11 or a portion of said exon having a length of at least one nucleotide excised therefrom. In another preferred embodiment, the polynucleotide corresponds to the sequence set forth in SEQ ID NO: 7 or a complement thereof which hybridizes under stringent conditions to the nucleotide sequence set forth in SEQ ID NO: 7. Preferably, the polynucleotide is in substantially pure form.

In another general aspect, the invention relates to isolated and purified biologically active polypeptide encoded by the above-described polynucleotides. In an especially preferred embodiment, the polypeptide has the amino acid sequence set forth in SEQ ID NO: 9. In preferred embodiments, the polypeptide has a purity of at least 99%.

In a further general aspect, the invention is directed to expression vectors each comprising a polynucleotide as described above operably linked to a promoter element that expresses the IRAK1c polypeptide encoded by the polynucleotide in a transfected host cell.

Additionally, the invention generally relates to recombinant host cells, which are transfected or transformed by an expression vector as described above and express the biologically active polypeptides.

In another general aspect, the invention relates to methods for performing assays to detect or diagnose a medical condition in a test biological sample, comprising: (a) measuring the expression level of IRAK1c in the biological sample; (b) measuring the expression level of IRAK1c in a control biological sample; and (c) comparing said expression level of IRAK1c in the test biological sample relative to expression level of IRAK1c in the control biological sample to diagnose or detect a medical condition mediated by modulation of Toll/interleukin-1 receptor signaling activity or IRAK1 activity. Such methods may be used to detect or diagnose medical conditions selected from inflammatory conditions, immunocompromised conditions, immunodeficiency conditions, hyperproliferative conditions, immunological conditions, neurological conditions, cancers, and ophthalmic conditions. In certain preferred embodiments, the measuring of IRAK1c expression comprises performing reverse transcriptase polymerase chain reaction using the IRAK1c-specific primers set forth in SEQ ID NO: 2 and SEQ ID NO: 3. The measurement of IRAK1c expression level may comprise performing immunoassay analysis. The test biological sample is preferably a tissue specimen obtained from a mammal, such as a human.

In an additional general aspect, the invention is directed to methods for identifying compounds having IRAK1c-modulating activity. The method comprises: (a) contacting an assay reagent comprising IRAK1c with a compound; (b) measuring the activity of IRAK1c in the presence of the compound to produce a test activity measurement, and measuring the activity of IRAK1c in the absence of the compound to produce a control activity measurement; and (c) comparing the test and control activity measurements, whereby a difference in such measurements identifies the compound as having IRAK1c-modulating activity. In some preferred embodiments, step (c) comprises detecting an alteration in IRAK1c mRNA levels, IRAK1c protein levels, secreted interleukin-6 levels, secreted tumor necrosis factor alpha levels, association with IRAK1, association with IRAK2, association with Tollip, association with MyD88, or association with TRAF6. The compound may be tested as a component of a solution, which may comprise a buffer.

Furthermore, the invention generally relates to methods for treating medical conditions mediated by modulation of Toll/interleukin-1 receptor signaling activity or IRAK1 activity. Such methods comprise administering to a subject a therapeutically effective amount of: a compound identified as having IRAK1c-modulating activity by the assay method described above; a pharmaceutically acceptable composition comprising an expression vector as described above; or an isolated and purified polypeptide having an amino acid sequence as set forth in SEQ ID NO: 9. In some preferred embodiments, the medical condition is selected from inflammatory conditions, immunocompromised conditions, immunodeficiency conditions, hyperproliferative conditions, immunological conditions, neurological conditions, cancers, and ophthalmic conditions. In other preferred embodiments, the medical condition is selected from adult respiratory disease syndrome, chronic obstructive pulmonary disease, pulmonary fibrosis, interstitial lung disease, lung adema, asthma, chronic cough, allergy, allergic rhinitis, immunological disorders associated with transplantation, rheumatoid arthritis, systemic lupus erythematosus, multiple sclerosis, diabetes, HIV infection, AIDS, solid tumors, skin cancers, lymphomas, hypotension, stroke, artherosclerosis, tachycardia, neurogenic inflammation, non-CD14 mediated sepsis, CD14 mediated sepsis, septic shock, osteoarthritis, osteoporosis, psoriasis, rash, contact and atopic dermatitis, Crohn's disease, ulcerative colitis, Behcet's syndrome, ankylosing spondylitis, sarcoidosis, gout, renal failure, and pain.

Other aspects, features and advantages of the invention will be apparent from the following disclosure, including the detailed description of the invention and its preferred embodiments and the appended claims.

BRIEF DESCRIPTION OF THE DRAWINGS

FIG. 1A shows a schematic diagram of the IRAK1 gene. Exons and introns are indicated by boxes and horizontal lines, respectively. The excision of all 237 bp of exon 11 (hatched box), which generates a preferred IRAK1c alternative splice variant, is indicated. FIG. 1B illustrates an anti-IRAK1 immunoblot, which depicts the molecular weight and expression level of endogenous IRAK1 in G292 cells after treatment with IL-1β compared to the molecular weight and expression level of myc-IRAK1c derived from myc-IRAK1c cDNA-transfected 293T cells. FIG. 1C illustrates a comparison of the expression profiles of IRAK1 and IRAK1c, spanning a variety of various tissues and cell types, as determined by RTPCR using splice variant-specific primers. RTPCR of G3PDH was used as a control. FIG. 1D depicts the detection of endogenous IRAK1c in two commercially available human brain lysate samples and THP-1 cells, as well as control transfected 293T cells. IRAK1 and IRAK1c were detected by anti-IRAK1 immunoblot analyses of total protein extracts.

FIGS. 2A-2E provide IRAK1 and IRAK1c sequences of oligonucleotide primers and polynucleotide cDNAs, and the polypeptide amino acid sequence of IRAK1c. FIG. 2A illustrates the oligonucleotide primers that were employed in polymerase chain reactions to generate the IRAK1 and IRAK1c cDNAs. SEQ ID NO: 1 is the sequence of the forward primer used to amplify IRAK1 transcripts by reverse transcriptase polymerase chain reaction (RTPCR). SEQ ID NO: 2 is the sequence of the forward primer used to amplify IRAK1c transcripts by reverse transcriptase polymerase chain reaction (RTPCR). SEQ ID NO: 3 is the sequence of the common reverse primer used to amplify both IRAK1 and IRAK1c transcripts. SEQ ID NO: 4 and SEQ ID NO: 5 correspond to the oligonucleotide sequences of the forward primer and reverse primer, respectively, used to generate the K239A mutant IRAK1 and IRAK1c cDNAs by site directed mutagenesis. SEQ ID NO: 5 corresponds to the sequence of the reverse primer used to generate the K239A mutant IRAK1 and IRAK1c cDNAs by site directed mutagenesis. FIG. 2B provides the human IRAK1 cDNA sequence (corresponding to Genbank accession number L76191), SEQ ID NO: 6; the portion corresponding to exon 11 of the genomic sequence is underlined. FIG. 2C provides the human IRAK1c splice variant cDNA sequence, SEQ ID NO: 7. FIG. 2D provides the polynucleotide sequence of IRAK1 exon 11, SEQ ID NO: 8. FIG. 2E provides the N-terminus to C-terminus amino acid sequence of human IRAK1c, SEQ ID NO: 9.

FIG. 3A illustrates a comparison of the in vitro kinase activity of the indicated myc-IRAK1 proteins immunoprecipitated from transfected 293T cells using the anti-myc antibody. The upper panel shows IRAK1 autophosphorylation and the lower panel depicts phosphorylation of an MBP substrate. FIG. 3B shows confirmation by anti-myc immunoblot analysis of the expression of the various myc-IRAK1 constructs used in FIG. 3A.

FIG. 4A illustrates the NFκB-luciferase reporter activity in 293T cells transfected with the indicated myc-IRAK1 or MyD88 plasmids and the PHTS-NFκB luciferase plasmid, followed by IL-1β stimulation or no stimulation, as indicated ("+" or "−", respectively). FIG. 4B demonstrates the verification or protein expression by anti-myc immunoblot analysis of whole cell extracts. FIG. 4C illustrates the percent inhibition in transfected 293T cells of NFκB-luciferase reporter activity as a function of increasing amounts of transfected myc-IRAK1c. FIG. 4D demonstrates the verification or protein expression by anti-myc immunoblot analysis of whole cell extracts. FIG. 4E illustrates the NFκB-luciferase reporter activity in G292 cells transfected with the indicated amounts of myc-IRAK1c or MyD88 plasmids and the PHTS-NFκB luciferase plasmid, followed by IL-1β no stimulation or stimulation, as indicated ("0 ng/ml" or "5 ng/ml"). FIG. 4F demonstrates the verification or protein expression by anti-myc immunoblot analysis of whole cell extracts. FIG. 4G illustrates the NFκB-luciferase reporter activity in G292 cells transfected with 250 ng of myc-IRAK1c, the indicated amounts of FLAG-TRAF6, and the pHTS-NFκB luciferase plasmid, followed by IL-1β no stimulation or stimulation, as indicated ("0 ng/ml" or "5 ng/ml").

FIG. 5A compares the level of IL-6 secretion in THP-1 cells that have been transfected with the various myc-IRAK1 constructs and either unstimulated (solid bars; "(−)") or stimulated with 50 ng/ml LPS for 12 hr (hatched bars; "(+)". Supernatants were analyzed for IL-6 levels by ELISA. Statistical significance (P value) was calculated by using the student T-test. FIG. 5B shows the level of TNFa secretion in THP-1 cells that have been transfected with either a myc-IRAK1c or an HA-IRAK1c construct and either unstimulated (solid bars; "(−)") or stimulated with 50 ng/ml LPS for 4 hr(hatched bars; "(+)". Supernatants were analyzed for TNFa levels by ELISA.

DETAILED DESCRIPTION OF THE INVENTION AND ITS PREFERRED EMBODIENTS

Figure 1A:
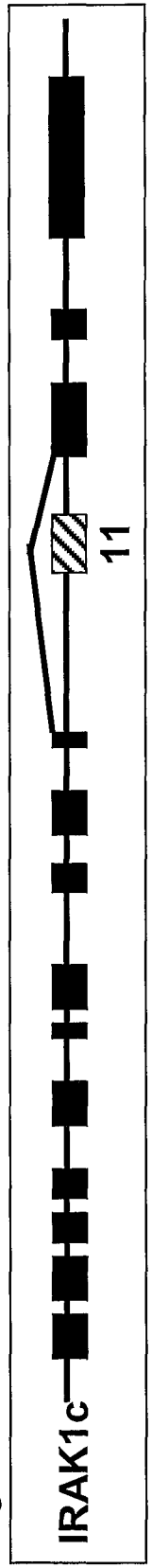
FIGS. 1A-1D illustrate alternative splicing of IRAK1 and expression of a preferred IRAK1c the variant.

All publications cited herein are hereby incorporated by reference. Unless defined herein or otherwise indicated below, all technical and scientific terms used herein have the same meaning as commonly understood in the art.

The following are abbreviations that are at times used in this specification below:
bp=base pair
cDNA=complementary DNA
IL-1b=interleukin 1 beta
IRAK=interleukin 1 receptor associated kinase
kb=kilobase; 1000 base pairs
kDa=kilodalton; 1000 dalton
MyD88=myeloid differentiation protein 88
NF-κB=nuclear factor-kappa B
nt=nucleotide
PAGE=polyacrylamide gel electrophoresis
PCR=polymerase chain reaction
SDS=sodium dodecyl sulfate
TIR=Toll/interleukin 1 receptor
TNFa=tumor necrosis factor alpha
Tollip=toll-interacting protein
TRAF6=tumor necrosis factor alpha receptor-associated factor 6

Additionally, the terms identified below have the defined meanings.

The terms "including," "comprising" and "containing" are used herein in their open, non-limiting sense.

As noted above, certain general embodiments of the invention relate to isolated and purified biologically active IRAK1c splice variants, polynucleotides that encode them, expression vectors comprising such polynucleotides, and recombinant host cells transfected or transformed by such vectors.

As used herein, "splice variant", "alternative splice variant", or "variant" means a polypeptide expressed from an mRNA transcript that is produced by processing of a precursor RNA (pre-RNA) species or a synthesized polypeptide corresponding thereto. In reference to the splice variant of the present invention, "IRAK1c" means a dominant negative IRAK1 splice variant.

An "isolated and purified biologically active" splice variant is a polypeptide that is substantially separate and free from contaminants, such that its biological activity is maintained. Exemplary contaminants include cellular material or other contaminating proteins (e.g., from the cell or tissue source when the polypeptide is produced and isolated from such sources), chemical precursors or other chemicals (e.g., when the polypeptide is chemically synthesized), or culture medium (e.g., when the polypeptide is recombinantly produced). For instance, in an exemplary embodiment when the splice variant is processed from cell or tissue sources, the polypeptide preparation preferably contains less than 5% (by dry weight) of contaminants. When the protein or biologically active portion thereof is recombinantly produced, it preferably contains less than 5% (by volume) of culture medium. When the polypeptide is produced by chemical synthesis, the preparation preferably contains less than 5% (by dry weight) of chemical precursors or compounds other than the splice variant. More preferably, the inventive splice variant has a purity of 99% or greater.

An "activity", a "biological activity", or a "functional activity" of a polypeptide or nucleic acid molecule refers to an activity exerted by the polypeptide or nucleic acid molecule as determined in vivo or in vitro according to standard techniques. Such activities can be a direct activity, such as an association with or an enzymatic activity on a second protein, or an indirect activity, such as a cellular signaling activity mediated by interaction of the protein with a second protein. Illustrative examples of biological activities of a dominant negative IRAK1c splice variant according to the invention include constitutive association with a TIR-associated protein, such as Tollip or MyD88, e.g., in the presence or absence of TIR-stimulating agents, and, e.g., the attenuation of downstream TIR-mediated signal transduction events.

Isolated biologically active polypeptides can have several different physical forms. The isolated polypeptide can exist as a full-length nascent or unprocessed polypeptide, or as partially processed polypeptides or combinations of processed polypeptides. The full-length nascent polypeptide can be post-translationally modified by specific proteolytic cleavage events that result in the formation of fragments of the full-length nascent polypeptide. A fragment, or physical association of fragments, can have the biological activity associated with the full-length polypeptide; however, the degree of biological activity associated with individual fragments can vary.

In a preferred embodiment of the invention, the IRAK1c is an isolated and purified biologically active polypeptide expressed from a polynucleotide having exon 11 or a portion thereof excised. The polynucleotide or nucleic acid molecule of the invention can be RNA or cDNA. In an especially preferred embodiment, the polynucleotide has the nucleotide sequence of SEQ ID NO: 7.

The term "nucleic acid" as used herein refers to a molecule comprised of one or more nucleotides, i.e., ribonucleotides, deoxyribonucleotides, or both. The term includes monomers and polymers of ribonucleotides (RNA) and deoxyribonucleotides (DNA), with the ribonucleotides and/or deoxyribonucleotides being bound together, in the case of the polymers, via 5' to 3' linkages. The ribonucleotide and deoxyribonucleotide polymers may be single- or double-stranded. However, linkages may include any of the linkages known in the art, including, for example, nucleic acids comprising 5' to 3' linkages. The nucleotides may be naturally occurring or may be synthetically produced analogs that are capable of forming base-pair relationships with naturally occurring base pairs. Examples of non-naturally occurring bases that are capable of forming base-pairing relationships include aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulfur, selenium, phosphorus, and the like.

As known in the art, alternative splicing sites may be found in intra-exon sequences of genes. Through routine experimentation alternative or cryptic splice junction sites may be found within exon 11 of the human IRAK1 gene, yielding a variety of IRAK1 transcripts, and used to ultimately produce other IRAK1c exon 11-variant polypeptides within the scope of the invention. It is also known that interspecies and interindividual polymorphic heterogeneity (genetic variation at a particular genetic locus among individuals in a population) in such intra-exonic alternative or cryptic splice junction sites can exist. Such heterogeneity can be exploited by the artisan to obtain various IRAK1c polypeptides with exon 11-encoding amino acid sequences of varying length that possess dominant negative biological activity as associated with deletion of the exon 11 in its entirety. Such alternative IRAK1c splice variants are therefore within the scope of the present invention.

Additionally, polynucleotides encoding alternative splice variants may be synthesized or selected by making use of the "redundancy" in the genetic code. Various codon substitutions, such as the silent changes that produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the encoded polypeptide, to change characteristics such as affinities for proteins with which the wild-type protein associates, affinities for antibodies, or degradation/turnover rates. Where alteration of a particular function is desired, insertions, deletions or non-conservative alterations can be engineered to produce polypeptides with altered functions but retained biological activity. Such functional alterations can, for example, alter one or more of the biochemical characteristics of the polypeptides of the invention so long as the desired biological activity is maintained. For example, appropriate alterations can be selected so as to generate polypeptides that are better suited for expression, scale up, and the like in the host cells chosen for expression.

Further embodiments provide engineered polynucleotides having any such nucleotide variations that are not known to occur naturally which encode polypeptides having properties that are different than, but still maintain the dominant negative biological activity of, naturally occurring human IRAK1c polypeptide. DNA sequences can be altered manually so as to code for a peptide having properties that are different from those of the naturally occurring peptide. Known methods of altering the DNA sequences include site-directed mutagenesis, chimeric substitution, and gene fusions. Site-directed mutagenesis may be used to change one or more DNA residues that can result in a silent mutation, a conservative mutation, or a nonconservative mutation. Chimeric genes may be prepared by swapping domains of similar or different genes to replace domains in the human IRAK1c gene. Similarly, fusion genes can be prepared that add domains to the human IRAK1c gene, such as an affinity tag to facilitate identification and isolation of the gene and protein.

The dominant negative biological activity of IRAK1c exon 11 splice variants, polymorphic variants, interspecies variants, as well as interspecies homologs and alleles, and engineered variants can be confirmed by examining, e.g., the IL-1/Toll receptor association, the NF-kB activating ability, or the MyD88 associating activity, of the putative IRAK1c polypeptide. For example, the dominant negative biological activity of the IRAK1 alternative splice variant polypeptide having an amino acid sequence of SEQ ID NO:9 can be used as a positive control in comparison to other IRAK1c splice variants to demonstrate the identification of a polymorphic biologically active dominant negative variant or allele of the IRAK1c protein or gene.

In an alternative embodiment, the IRAK1c is a biologically active polypeptide having at least 95% sequence identity to the amino acid sequence set forth in SEQ ID NO: 9, or that is encoded by a polynucleotide having 95% sequence identity to the nucleotide sequence set forth in SEQ ID NO: 7 or a complement thereof.

"Sequence identity" or similarity, as known in the art, is the relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

To determine the percent identity or similarity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same or similar amino acid residue or nucleotide as the corresponding position in the second sequence, then the molecules are identical or similar at that position.

Both identity and similarity can be readily calculated. In calculating percent identity, only exact matches are counted. Methods commonly employed to determine identity or similarity between sequences include, e.g., those disclosed in Carillo et al. (1988), SIAM J. Applied Math. 48, 1073. Preferred methods to determine identity are designed to give the largest match between the sequences tested. Methods to determine identity and similarity are embodied in computer programs. A preferred example of a mathematical algorithm utilized for the comparison of two sequences is the algorithm of Karlin et al. (1990), *Proc. Natl. Acad. Sci. USA* 87:2264-2268, modified as in Karlin et al. (1993), *Proc. Natl. Acad. Sci. USA* 90:5873-5877. Such an algorithm is incorporated into the NBLAST and XBLAST programs of Altschul et al. (1990), *J Mol. Biol* 215:403-410. To obtain gapped alignments for comparison purposes, Gapped BLAST can be utilized as described in Altschul et al. (1997), *Nucleic Acids Res.* 25:3389-3402. Alternatively, PSI-Blast can be used to perform an iterated search, which detects distant relationships between molecules. When utilizing BLAST, Gapped BLAST, and PSI-Blast programs, the default parameters of the respective programs (e.g., XBLAST and NBLAST) can be used. Additionally, there is the FASTA method (Atschul et al. (1990), *J. Molec. Biol.* 215, 403), which can also be used. Another preferred example of a mathematical algorithm useful for the comparison of sequences is the algorithm of Myers et al. (1988), *CABIOS* 4:11-17. Such an algorithm is incorporated into the ALIGN program (version 2.0), which is part of the GCG sequence alignment software package (Devereux et al. (1984), *Nucleic Acids Research* 12(1), 387). Yet another preferred example of a mathematical algorithm useful for comparison of sequences is the algorithm, PILEUP, which creates a multiple sequence alignment from a group of related sequences using progressive, pairwise alignments to show relationship and percent sequence identity, and uses a simplification of the progressive alignment method of Feng & Doolittle, *J. Mol. Evol.* 35:351-360 (1987). The method used is similar to the method described by Higgins & Sharp, *CABIOS* 5:151-153 (1989). PILEUP can be obtained from the GCG sequence analysis software package, e.g., version 7.0 (Devereaux et al., *Nuc. Acids Res.* 12:387-395 (1984)).

In another preferred embodiment, the IRAK1c polypeptide is encoded by a polynucleotide specifically hybridizing under stringent hybridization conditions to a nucleic acid molecule having the nucleotide sequence set forth in SEQ ID NO: 7. The terminology "specifically hybridizing" refers to the binding, duplexing, or hybridizing of a molecule only to a particular nucleotide sequence under stringent hybridization conditions when that sequence is present in a complex mixture (e.g., total cellular or library DNA or RNA).

"Stringent hybridization conditions" has the meaning known in the art. An extensive guide to the hybridization of nucleic acids is found in Sambrook et al., Molecular Cloning: A Laboratory Manual, Second Edition, Cold Spring Harbor Laboratory, Cold Spring Harbor, N.Y., and (1989) Tijssen, Techniques in Biochemistry and Molecular Biology-Hybridization with Nucleic Probes, "Overview of principles of hybridization and the strategy of nucleic acid assays" (1993). Stringent hybridization conditions may be suitably selected in view of the particular sequence.

Longer sequences hybridize specifically at higher temperatures. Exemplary stringent conditions include a temperature about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Exemplary stringent conditions further include a salt concentration less than about 1.0 M sodium ion, e.g., about 0.01 to 1.0 M sodium ion concentration (or other salts) at pH 7.0 to 8.3 and a temperature of at least about 30° C for short probes (e.g., 10 to 50 nucleotides) and at least about 60° C. for long probes (e.g., greater than 50 nucleotides). Stringent conditions may also include the addition of destabilizing agents such as formamide. For selective or specific hybridization, an exemplary positive signal is at least two times background, optionally 10 times background hybridization. Illustrative stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes.

In a preferred embodiment, the IRAK1c polynucleotide has the nucleotide sequence set forth in SEQ ID NO: 7 or is a complement thereof. In an especially preferred embodiment the IRAK1 polynucleotide is in substantially pure form.

The term "a substantially pure form" as used herein in reference to a polynucleotide means that the polynucleotide is essentially free of contaminating matter that would interfere with properties or characteristics of the polynucleotide essential for the encoding of the biologically active dominant negative IRAK1c splice variant. Substantially pure forms of polynucleotides may be produced by, e.g., isolation or purification techniques.

In an especially preferred embodiment of the polypeptide of the invention, the IRAK1c splice variant has the amino acid sequence set forth in SEQ ID NO: 9. Other exemplary embodiments of the inventive polypeptide include active fragments or derivatives of the human IRAK1c splice variant, such as those obtained through routine techniques such as amino acid insertions, deletions, and substitutions, created using recombinant DNA techniques.

An "active fragment or derivative" of IRAK1c means a fragment or derivative of an IRAK1c protein that maintains the dominant negative biological activity of the full-length IRAK1c (SEQ ID NO: 9). Biological activity of an IRAK1c active fragment can be evidenced, for example, by an attenuation of TIR-mediated signaling events, such as by constitutive association with a Tollip or a MyD88 protein, i.e., in both the presence and absence of TIR activating agents. The biological activity can also be reflected by disenabling TIR activating agents to affect activation of NF-kB or any other downstream target of TIR-mediated signaling.

It is within the purview of one of ordinary skill in the art to determine which amino acid residues or nucleotides may be added, deleted, or replaced in the full-length polypeptide or polynucleotide encoding it without abolishing biological activities of interest, such as TIR signaling modulatory activity, to obtain suitable fragments or derivatives. For example, the sequence of the particular polypeptide fragment or derivative may be compared with that of similar peptides to determine residues or regions of homology that need to be conserved to maintain activity.

Suitable amino acid substitutions may be determined by replacing one amino acid with another amino acid having similar structural and/or chemical properties, i.e., by making conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Suitable variations may be routinely determined by experimentally making insertions, deletions, or substitutions of amino acids in a polypeptide molecule using recombinant DNA techniques and assaying the resulting recombinant variants for activity.

Additional illustrative protein modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, sumoylation, transfer-RNA mediated addition of amino acids to proteins such as arginylation, and ubiquitination. Procedures for making several common modifications, such as glycosylation, lipid attachment, sulfation, gamma-carboxylation of glutamic acid residues, hydroxylation and ADP-ribosylation, are described in many basic texts, including PROTEINS—STRUCTURE AND MOLECULAR PROPERTIES, $2^{nd}$ Ed., T. E. Creighton, W. H. Freeman and Company, New York (1993). Many detailed reviews are also available on this subject, such as those provided by Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York (1983); Seifter et al. (1990), *Meth. Enzymol.* 182, 626-646; and Rattan et al., "Protein Synthesis: Posttranslational Modifications and Aging", (1992) *Ann. N.Y. Acad. Sci.* 663, 48-62.

It will be appreciated that, as is known, polypeptides can be linear or non-linear (e.g., branched or cyclic). For instance, polypeptides can be post-translationally modified, including via natural processing, or through human manipulation. Circular, branched and branched-circular polypeptides can be synthesized by non-translation natural processes and by entirely synthetic methods as well. Modifications can occur anywhere in a polypeptide, including the peptide backbone, the amino acid side-chains and the amino or carboxyl termini. For example, blockage of the amino or carboxyl group or both in a polypeptide by a covalent modification is common in naturally occurring and synthetic polypeptides, and such modifications can be present in polypeptides of the present invention. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus can be deleted. Accordingly, this invention contemplates both the methionine-containing and the methionineless amino terminal variants of the protein.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is known, glycosylation often does not occur in bacterial hosts such as, for example, *E. coli*. Accordingly, when glycosylation is desired, a polypeptide should be expressed in a glycosylating host, generally a eukaryotic cell. Insect cells often carry out the same post-translational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification can be present in the same or varying degree at several sites in a given polypeptide.

In various embodiments, IRAK1c polynucleotides are inserted into expression vectors for introduction of such polynucleotides into host cells for the expression, i.e., production of the encoded mRNA or protein, of the IRAK1c polypeptides encoded by such polynucleotides in such host cells. The expressed IPAK1c polypeptides from the resulting recombinant host cells are isolated for various uses in viLro, or serve to modulate various other in vivo activities within such recombinant host cells.

A host cell, which is a cell that contains a DNA molecule either in a vector or integrated into a cell chromosome, can be either a native host cell that contains the DNA molecule endogenously, or a recombinant host cell. Exemplary host cells include bacterial cells, yeast cells, and animal cells. Preferred host cells include mammalian cells, more preferably human cells.

One exemplary embodiment of a host cell is a recombinant host cell, which is a cell that has been transformed or transfected by an exogenous DNA sequence. A cell has been transformed by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA. Recombinant host cells may be prokaryotic or eukaryotic, including bacteria such as *E. coli*, fungal cells such as yeast, mammalian cells such as cell lines of human, bovine, porcine, monkey and rodent origin, and insect cells such as *Drosophila* and silkworm derived cell lines. A recombinant host cell refers not only to the particular subject cell, but also to the progeny or potential progeny of such a cell. Because certain modifications can occur in succeeding generations due to either mutation or environmental influences, such progeny may not, in fact, be identical to the parent cell, but are still intended to be included within the scope of the term.

A clone is a population of cells derived from a single cell or common ancestor by mitosis. A cell line is a clone of a primary cell that is capable of stable growth in vitro for many generations.

Vectors of the present invention also include specifically designed expression systems that allow the shuttling of DNA between hosts, such as bacteria-yeast or bacteria-animal cells or bacteria-fungal cells or bacteria-invertebrate cells. Numerous cloning vectors are known to those skilled in the art and the selection of an appropriate cloning vector is within the purview of the artisan. For other suitable expression systems for both prokaryotic and eukaryotic cells see, e.g., chapters 16 and 17 of Maniatis et al., supra.

To obtain high level expression of a cloned gene or nucleic acid, such as a cDNA encoding an IRAK1c polypeptide, an IRAK1c sequence is preferably subcloned into an expression vector that contains a strong promoter to direct transcription, a transcription/translation terminator, and if for a nucleic acid encoding a protein, a ribosome binding site for translational initiation. Suitable bacterial promoters are well known in the art and are described, e.g., in Sambrook et al. and Ausubel et al. Bacterial expression systems for expressing the IRAK1c proteins disclosed in the present invention are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are known in the art and are also commercially available. In exemplary embodiments, the eukaryotic expression vector is an adenoviral vector, an adeno-associated vector, or a retroviral vector.

The promoter used to direct expression of a heterologous IRAK1c-encoding polynucleotide depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector generally contains a transcription unit or expression cassette that contains all the additional elements required for the expression of the IRAK1c-encoding polynucleotide in host cells. An exemplary expression cassette contains a promoter operably linked to the polynucleotide sequence encoding an IRAK1c polypeptide, and signals required for efficient polyadenylation of the transcript, ribosome binding sites, and translation termination. The polynucleotide sequence encoding an IRAK1c polypeptide may be linked to a cleavable signal peptide sequence to promote secretion of the encoded protein by the transfected cell. Exemplary such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette can also contain a transcription termination region downstream of the structural gene to provide for efficient termination. The termination region may be obtained from the same gene as the promoter sequence or may be obtained from different genes.

In exemplary embodiments, any of the conventional vectors used for expression in eukaryotic or prokaryotic cells may be used. Standard bacterial expression vectors include plasmids such as pBR322-based plasmids, pSKF, pET23D, and fusion expression systems such as GST and LacZ. Examples of mammalian expression vectors include, e.g., pCDM8 (Seed (1987), Nature 329:840) and pMT2PC (Kaufinan et al., (1987), *EMBO J* 6:187-195). Commercially available mammalian expression vectors which can be suitable for recombinant IRAK1c expression include, for example, pMAMneo (Clontech), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

In yet other exemplary embodiments, the recombinant mammalian expression vector is capable of directing expression of the nucleic acid preferentially in a particular cell type (e.g., tissue-specific regulatory elements are used to express the nucleic acid). Various tissue-specific regulatory elements are known in the art. Examples of suitable tissue-specific promoters include the albumin promoter (liver-specific; Pinkert et al. (1987), *Genes Dev.* 1:268-277), lymphoid-specific promoters (Calame et al. (1988), *Adv. Immunol.* 43:235-275), such as promoters of T cell receptors (Winoto et al. (1989), *EMBO J* 8:729-733), and immunoglobulins (BaneiJi et al. (1983), *Cell* 33:729-740; Queen et al., (1983), *Cell* 33:741-748), neuron-specific promoters (e.g., the neurofilament promoter; Byme et al. (1989), *Proc. Natl. Acad. Sci. USA* 86:5473-5477), pancreas-specific promoters (Edlund et al. (1985), *Science* 230:912-916), and mammary gland-specific promoters (e.g., milk whey promoter; U.S. Pat. No. 4,873,316 and European Patent Publication No. 264,166). Developmentally regulated promoters also include, for example, the marine hox promoters (Kessel et al. (1990), *Science* 249:374-379) and the beta-fetoprotein promoter (Campes et al. (1989), *Genes Dev.* 3:537-546).

Epitope tags can also be added to recombinant proteins to provide convenient methods of isolation, e.g., c-myc, hemoglutinin (HA)-tag, 6-His tag, maltose binding protein, VSV-G tag, or anti-FLAG tag, and others well known to those of skill in the art.

Expression vectors containing regulatory elements from eukaryotic viruses can be used in eukaryotic expression vectors, e.g., SV40 vectors, papilloma virus vectors, and vectors derived from Epstein-Barr virus. Other exemplary eukaryotic vectors include PMSG, pAV009/A+, pMTO10/A+, pMAMneo 5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification, such as neomycin, thymidine kinase, hygromycin B phosphotransferase, and dihydrofolate reductase. Alternatively, high yield expression systems not involving gene amplification are also suitable, such as using a baculovirus vector in insect cells, with a sequence encoding an IRAK1c polypeptide under the direction of the polyhedrin promoter or other strong baculovirus promoters.

The elements that can be included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences may be chosen such that they do not interfere with the replication of the DNA in eukaryotic cells, if necessary or desired.

In preferred embodiments, the pCDNA3.1 (Invitrogen), pFASTBac (Invitrogen), and MscvPuro (BD Biosciences) expression vectors are employed to introduce the IRAK1c polynucleotides of the present invention into host cells and to express them in transformed or transfected cells.

Standard transfection methods may be used to produce bacterial, mammalian, yeast or insect cell lines that express large quantities of an IRAK1c polypeptide, which are then purified using standard techniques (see, e. g., Colley et al., *J. Biol. Chem.* 264:17619-17622 (1989); Guide to Protein Purification, in *Methods in Enzyimology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983)).

Any of the known procedures suitable for introducing foreign nucleotide sequences into host cells may be used to introduce the expression vector. These include the use of reagents such as Superfect (Qiagen), liposomes, calcium phosphate transfection, polybrene, protoplast fusion, electroporation, microinjection, plasmid vectors, viral vectors, biolistic particle acceleration (the Gene Gun), or any other known methods for introducing cloned genomic DNA, cDNA, synthetic DNA or other foreign genetic material into a host cell (see, e. g., Sambrook et al., supra). The selected particular genetic engineering procedure used should be capable of successfully introducing at least one gene into the host cell capable of expressing an IRAK1c mRNA, cDNA, or gene.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) may be introduced into the host cells along with the gene of interest. Preferred selectable markers include those which confer resistance to drugs, such as G418, puromycin, hygromycin and methotrexate. Cells stably transfected with the introduced nucleic acid can be identified by drug selection (e.g., cells that have incorporated the selectable marker gene will survive, while the other cells die).

A heterologous regulatory element can be inserted into a stable cell line or cloned microorganism, such that it is operatively linked with and activates expression of endogenous genes, using techniques such as targeted homologous recombination, e.g., as described in U.S. Pat. No. 5,272,071 and WIPO Publication No. WO 91/06667.

After the expression vector is introduced into the cells, the transfected cells are cultured under conditions favoring expression of the IRAK1c polypeptide, which is recovered from the culture using standard techniques identified below. Methods of culturing prokaryotic or eukaryotic cells are known and are taught, e.g., in Ausubel et al., Sambrook et al., and in Freshney, CULTURE OF ANIMAL CELLS, 3d. Ed., (1993), Wiley-Liss (publisher).

The isolated and purified IRAK1c polypeptides of the present invention may be used in assay methods for detecting or diagnosing medical conditions in test biological samples and in methods for identifying compounds having IRAK1c-modulating activities.

In preferred embodiments of such methods, naturally occurring IRAK1c polypeptides are isolated and purified, e.g., from mammalian tissue such as brain, spleen, placenta, lung, liver, kidney, pancreas, prostate, testis, ovary, small intestine, colon, lymph node, and tonsils, or any other source of an IRAK1c homolog. Bodily fluids such as blood, blood plasma, serum, seminal fluid, urine, or any other mammalian bodily fluid can also serve as sources of natural IRAK1c polypeptides. Cultured mammalian cell lines are still further exemplary sources of natural IRAK1c polypeptides.

In especially preferred embodiments, IRAK1c is derived from human brain tissue, liver tissue, from the human cancer cell lines, G292 (ATCC #CRL-1423), HeLa (ATCC #CCL-2), Jurkat (ATCC #TIB-152),and THP-1 (ATCC #TIB-20). In still other preferred embodiments, IRAK1c polypeptides are derived from monocytes substantially purified from peripheral blood and from monocyte-derived dendritic cells. Methods of purification of monocytes substantially purified from peripheral blood are known in the art; for example, such cells may be adsorbed onto CD14 microbeads and subsequently separated on an Auto Macs (Miltenyi Biotech). An exemplary method to derive dendritic cells from monocytes is to culture the monocytes in the presence of GM-CSF and IL-4 in endotoxin-free media and reagents.

In other embodiments, recombinant IRAK1c polypeptides may be purified from any suitable bacterial or eukaryotic expression system, e.g., those described supra. IRAK1c proteins may be purified by standard techniques, including selective precipitation with such substances as ammonium sulfate; column chromatography; and immunopurification methods (see, e.g., Scopes, PROTEIN PURIFICATION: PRINCIPLES AND PRACTICE (1982); U.S. Pat. No. 4,673,641; Ausubel et al., supra; and Sambrook et al., supra).

A number of procedures can be employed when recombinant IRAK1c polypeptide is being purified. For example, proteins having established molecular adhesion properties can be reversibly fused to the IRAK1c polypeptide. With the appropriate ligand, an IRAK1c polypeptide can be selectively adsorbed to a purification column and then freed from the column in a relatively pure form. The fused protein is then removed by enzymatic activity. IRAK1c proteins can also be purified using immunoaffinity columns.

Recombinant proteins may be expressed by transformed bacteria or eukaryotic cells in large amounts, preferably after promoter induction; but expression can be constitutive. Promoter induction with IPTG is one example of an inducible promoter system. Cells may be grown according to standard procedures in the art. Fresh or frozen cells may be used for isolation of protein.

Proteins expressed in bacteria may form insoluble aggregates (inclusion bodies). Several known protocols are suitable for purification of IRAK1c inclusion bodies. For example, purification of inclusion bodies may involve the extraction, separation and/or purification of inclusion bodies by disruption of bacterial cells, e.g., by incubation in a buffer of 50 mM TRIS/HCL pH 7.5, 50 mM NaCl, 5 mM MgCl2, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria will be apparent to those of ordinary skill in the art (see, e.g., Sambrook et al., supra; Ausubel et al., supra).

If necessary or desired, the inclusion bodies may be solubilized, and the lysed cell suspension centrifuged to remove unwanted insoluble matter. Proteins that formed the inclusion bodies may be renatured by dilution or dialysis with a compatible buffer. Suitable solvents include urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known in the art. IRAK1c polypeptides are separated from other bacterial proteins by standard separation techniques, e.g., with Ni-NTA agarose resin.

Alternatively, it is possible to purify IRAK1c polypeptides from bacteria periplasm. After lysis of the bacteria, when an IRAK1c protein is exported into the periplasm of the bacteria, the periplasmic fraction of the bacteria can be isolated by cold osmotic shock or another method known in the art. To isolate recombinant proteins from the periplasm, the bacterial cells may be centrifuged to form a pellet. The pellet may be resuspended in a buffer containing 20% sucrose. To lyse the cells, the bacteria may be centrifuged and the pellet resuspended in ice-cold 5 MM MgSO$_4$ and kept in an ice bath for approximately 10 minutes. The cell suspension may be centrifuged and the supernatant decanted and saved. The recombinant proteins present in the supernatant can be separated from the host proteins by standard separation techniques known in the art.

As an initial step, e.g., if a protein mixture is complex, an initial salt fractionation can be used to separate many of the unwanted host cell proteins (or proteins derived from the cell culture media) from the recombinant protein of interest. An exemplary salt is ammonium sulfate, which precipitates proteins by effectively reducing the amount of water in the protein mixture. Proteins then precipitate on the basis of their solubility. The more hydrophobic a protein is, the more likely it is to precipitate at lower ammonium sulfate concentrations. An exemplary isolation protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed to achieve the desired purity, e.g., through dialysis or diafiltration. Other known methods that rely on solubility of proteins, such as cold ethanol precipitation, can be used to fractionate complex protein mixtures.

In other examples, the molecular weight of an IRAK1c splice variant can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut-off greater than the molecular weight of the protein of interest. The recombinant protein will pass through the membrane into the filtrate. The filtrate can then be chromatographed.

IRAK1c proteins can also be separated from other proteins on the basis of net surface charge, hydrophobicity, and affinity for heterologous molecules. In addition, antibodies raised against proteins can be conjugated to column matrices and the proteins immunopurified. All of these methods are known in the art. It will be apparent to those of ordinary skill in the art that chromatographic techniques can be performed at any suitable scale and using equipment from many different manufacturers (e.g., Pharmacia Biotech).

The invention is also directed to antibodies that specifically bind to IRAK1c polypeptides. Because the amino acid sequence of IRAK1c variants are analogous to amino acid sequences of the full length IRAK1c polypeptide, antibodies that recognize the full length IRAK1 polypeptide may also recognize IRAK1c splice variants. However, immunogenic amino acid sequences exposed in IRAK1c polypeptides, which are not exposed in the IRAK1 full length polypeptide, can be exploited to generate IRAK1c-specific antibodies.

Such IRAK1- and IRAK1c-specific antibodies have numerous applications, including for the modulation of IRAK1c dominant negative activity and for immunoassays to detect IRAK1c alternative splice variants. Immunoassays can be used to qualitatively or quantitatively analyze IRAK1c polypeptides. A general overview of such technology can be found in Harlow & Lane, ANTIBODIES: A LABORATORY MANUAL (1988).

Methods of producing polyclonal and monoclonal antibodies that react specifically with IRAK1c polypeptides are known in the art (see, e.g., Coligan, CURRENT PROTOCOLS IN IMMUNOLOGY (1991); Harlow & Lane, supra; Goding, MONOCLONAL ANTIBODIES: PRINCIPLES AND PRACTICE (2d ed. 1986); and Kohler & Milstein, Nature 256:495-497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)).

A number of IRAK1c-comprising immunogens may be used to produce antibodies specifically reactive with an IRAK1c polypeptide. For example, a recombinant IRAK1c protein, or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those working in the art. In one exemplary method, an inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the IRAK1c polypeptide. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. To illustrate briefly, spleen cells from an animal immunized with a desired antigen are immortalized, e.g., by fusion with a myeloma cell (see Kohler & Milstein, Eur. J Immunol. 6:511-519 (1976)). Alternative methods of immortalization include transformation with Epstein Barr Virus, oncogenes, or retroviruses. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., Science 246:1275-1281 (1989).

Monoclonal antibodies and polyclonal sera may be collected and titered against the immunogen protein in an immunoassay, for example, a solid phase immunoassay with the immunogen immobilized on a solid support. To illustrate, polyclonal antisera with a titer of $10^4$ or greater are selected and tested for their cross-reactivity against non-IRAK1c proteins, or even related proteins from other organisms, using a competitive binding immunoassay. Specific polyclonal antisera and monoclonal antibodies may bind with a Kd of 1 µM, 0.1 µM or 0.01 µM or better.

Using either IRAK1-specific or IRAK1c-specific antibodies, individual IRAK1c proteins can be detected by a variety of immunoassay methods. For a review of immunological and immunoassay procedures, see BASIC AND CLINICAL IMMUNOLOGY (Stites & Terr eds., 7th ed. 1991). Moreover, immunoassays can be performed in any of several configurations, which are reviewed extensively in ENZYME IMMUNOASSAY (Maggio, ed., 1980); and Harlow & Lane, supra.

IRAK1c proteins can be detected and/or quantified using any of a number of known immunological binding assays (see, e.g., U.S. Pat. Nos. 4,366,241; 4,376,110; 4,517,288; and 4,837,168). For a review of the general immunoassays, see also METHODS IN CELL BIOLOGY: ANTIBODIES IN CELL BIOLOGY, volume 37 (Asai, ed. 1993); BASIC AND CLINICAL IMMUNOLOGY (Stites & Terr, eds., 7th ed. 1991). Immunological binding assays (or immunoassays) generally use an antibody that specifically binds to a protein or antigen of choice (in this case an IRAK1c polypeptide or an antigenic subsequence thereof). The antibody (e.g., anti-IRAK1, or anti-IRAK1c) may be produced by any suitable means known in the art.

Immunoassays also may employ a labeling agent to specifically bind to and label the complex formed by the antibody and antigen. The labeling agent may itself be one of the moieties comprising the antibody/antigen complex. Thus, the labeling agent may be a labeled IRAK1c polypeptide or a labeled anti-IRAK1 or anti-IRAK1c antibody. Alternatively, the labeling agent may be a third moiety, such a secondary antibody, that specifically binds to the antibody/IRAK1c complex (a secondary antibody is preferably specific to antibodies of the species from which the first antibody is derived). Other proteins capable of specifically binding immunoglobulin constant regions, such as protein A or protein G, may be used as the label agent. These proteins exhibit a strong non-immunogenic reactivity with immunoglobulin constant regions from a variety of species (see, e.g., Kronval et al., *J. Immunol.* 111: 1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are known in the art.

Throughout the assays, incubation and/or washing steps may be appropriate after each combination of reagents. Incubation steps can vary from about 5 seconds to several hours, optionally from about 5 minutes to about 24 hours. However, the incubation time will depend upon the assay format, antigen, volume of solution, concentrations, and the like. The assays may be carried out at ambient temperature, although they can be conducted over a range of temperatures, such as 10° C. to 40° C.

Immunoassays for detecting an IRAK1c protein in a sample may be either competitive or noncompetitive. Noncompetitive immunoassays are assays in which the amount of antigen is directly measured. In one preferred sandwich assay, for example, the anti-IRAK1 or anti-IRAK1c antibodies can be bound directly to a solid substrate on which they are immobilized. These immobilized antibodies then capture the IRAK1c protein present in the test sample. The IRAK1c protein thus immobilized is then bound by a labeling agent, such as a second IRAK1 or IRAK1c antibody bearing a label. Alternatively, the second antibody may lack a label, but it may, in turn, be bound by a labeled third antibody specific to antibodies of the species from which the second antibody is derived. The second or third antibody is often modified with a detectable moiety, such as biotin, to which another molecule specifically binds, e.g., streptavidin, to provide a detectable moiety.

In competitive assays, the amount of IRAK1c protein present in the sample may be measured indirectly by measuring the amount of a known, added (exogenous) IRAK1c protein displaced (competed away) from an anti-IRAK1 or anti-IRAK1c antibody by the unknown IRAK1c protein present in a sample. In one exemplary competitive assay, a known amount of IRAK1c protein is added to a sample and the sample is then contacted with an antibody that specifically binds to the IRAK1c protein. The amount of exogenous IRAK1c protein bound to the antibody is inversely proportional to the concentration of IRAK1c protein present in the sample. In an exemplary embodiment, the antibody is immobilized on a solid substrate. The amount of IRAK1c protein bound to the antibody may be determined either by measuring the amount of IRAK1c protein present in an IRAK1c/antibody complex, or alternatively by measuring the amount of remaining uncomplexed protein. The amount of IRAK1c protein may be detected by providing a labeled IRAK1c molecule.

A hapten inhibition assay is another illustrative competitive assay. In this assay the known IRAK1c protein is immobilized on a solid substrate. A known amount of anti-IRAK1 or anti-IRAK1c antibody is added to the sample, and the sample is then contacted with the immobilized IRAK1c. The amount of anti-IRAK1 or anti-IRAk1c antibody bound to the known immobilized IRAK1c protein is inversely proportional to the amount of IRAK1c protein present in the sample. Again, the amount of immobilized antibody may be determined by detecting either the immobilized fraction of antibody or the fraction of the antibody that remains in solution. Detection may be direct where the antibody is labeled or indirect by the subsequent addition of a labeled moiety that specifically binds to the antibody as described above.

Nucleic acid assays may also be used to detect for the presence of DNA and RNA for an IRAK1c polynucleotide in a sample. Exemplary embodiments include suitable techniques known in the art such as Southern analysis, Northern analysis, dot blots, RNase protection, S 1 analysis, amplification techniques such as PCR and LCR, RTPCR, and in situ hybridization. In in situ hybridization, the target nucleic acid is liberated from its cellular surroundings in such a way as to be available for hybridization within the cell while preserving the cellular morphology for subsequent interpretation and analysis. See also, Singer et al., *Biotechniques* 4:230-250 (1986); Haase et al., *Methods in Virology,* vol. VII, pp. 189-226 (1984); and NUCLEIC ACID HYBRIDIZATION: A PRACTICAL APPROACH (Hames et al., eds. 1987).

For example, using cDNA or genomic DNA libraries, or total mRNA from suitable cells as a template and appropriate oligonucleotide primers, a nucleic acid molecule of the invention can be amplified according to standard PCR amplification techniques. The amplified nucleic acid can be cloned into an appropriate vector and characterized by DNA sequence analysis.

Another illustrative method to isolate a nucleic acid molecule of the invention is to probe a genomic or cDNA library, or total mRNA with one or more natural or artificially designed probes using procedures recognized by those skilled in the art. See, e.g., CURRENT PROTOCOLS IN MOLECULAR BIOLOGY, Ausubel et al. (eds.), Greene Publishing Association and John Wiley Interscience, New York, 1989, 1992. Probes are preferably labeled with an analytically detectable reagent to facilitate detection. Useful reagents include, e.g., radioisotopes, fluorescent dyes, or enzymes capable of catalyzing the formation of a detectable product. The probes enable the artisan to isolate complementary copies of genomic DNA, cDNA or RNA polynucleotides encoding human IRAK1c. Similar routine procedures can also be used to isolated nucleic acid molecules encoding IRAK1c proteins from other animal sources or to screen such sources for related sequences, e.g., additional members of the family, type and/or subtype, including transcriptional regulatory and control elements as well as other stability, processing, translation and tissue specificity-determining regions from 5' and/or 3' regions relative to the coding sequences disclosed herein.

An alternative method to prepare nucleic acid molecules corresponding to all or a portion of a nucleic acid molecule of the invention is by standard synthetic techniques, e.g., using an automated DNA synthesizer.

Construction of genomic DNA libraries, preparation of cDNA libraries, or isolation of total MRNA from the identified source cell can be performed by standard techniques known in the art. These techniques can be found, for example, in Maniatis et al., MOLECULAR CLONING: A LABORATORY MANUAL, Second Edition (Cold Spring Harbor Laboratory, Cold Spring Harbor, New York, 1989).

In certain preferred embodiments, the oligonucleotides corresponding to the nucleotide sequences disclosed in SEQ ID NO: 2 and SEQ ID NO: 3 are used as primers for reverse transcriptase (RT) PCR amplification and detection of IRAK1c transcripts. The primers can be prepared by standard synthetic techniques, e.g., using an automated DNA synthesizer.

In other exemplary embodiments, IPAK1c polynucleotides are detected using the hybridization-based methods disclosed supra to determine, e.g., IRAK1c RNA levels or to detect particular DNA sequences, e.g., for genotyping or for forensic applications. For example, gene expression of IRAK1c can be analyzed by techniques known in the art, e.g., Northern blotting, reverse transcription and amplification of mRNA, dot blotting, in situ hybridization, RNase protection, probing DNA microchip arrays, and the like. In a preferred exemplary embodiment, high density oligonucleotide analysis technology (e.g., GeneChip®) is used to identify homologous and polymorphic fragments or derivatives of IRAK1c, or to monitor levels of IRAK1c mRNA. In the case where a homolog is linked to a known disease, they can be used with GeneChip® as a diagnostic tool in detecting the disease in a biological sample, see, e. g., Gunthand et al., *AIDS Res. Hum. Retroviruses* 14:869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998). In still further exemplary embodiments, e.g., to detect tissue specific or temporal patterns of gene expression, an IRAK1c polynucleotide is detected using in situ hybridization.

In one general embodiment of the present invention, a method is provided for performing an assay to detect or diagnose a medical condition in a test biological sample comprising measuring the expression level of IRAK1c in the test biological sample relative to the expression level of IRAK1c in a control sample for the purposes of diagnosing or detecting a medical condition mediated by modulation of IRAK1c activity or Toll/interleukin-1 receptor signaling activity.

Exemplary test biological samples include cell samples, tissue specimens, bodily fluid, biopsy samples, crude cellular extracts, substantially purified cellular extracts, and cell fractions. A test biological sample can also be a whole organism, or it can be a sample or specimen from an animal, preferably, a mammal, or more preferably a human.

Diagnosis or detection of a medical condition includes determining the identity, presence, or degree of severity of a medical condition, or determining or detecting a predisposition or susceptibility for a medical condition, or prognosticating a medical condition.

A "medical condition" means a disease, disorder, pathology, syndrome, or ailment associated with overactivity or insufficient activity of one or more TIR signaling events, or a symptom or pathological condition accompanying such a disorder, disease, pathology, syndrome, or ailment.

In another general embodiment, the invention provides an assay method for identifying compounds that modulate IRAK1c activity. "Modulation of IRAK1c activity" includes stimulation, inhibition, enhancement, suppression, activation, repression, coactivation, corepression, antagonism, agonism, or other alteration of IRAK1c activity. Modulation of IRAK1c activity can be accomplished, for example, through IRAK1c transcriptional regulation by other polypeptides and the genes that encode them, whereby IRAK1c mRNA levels are modulated; IRAK1c polypeptide expression regulation, which includes modulation of the rate of IRAK1c translation, post-translational processing, and proteosomal or proteolytic degradation; modulation of TIR- or IRAK1c-signaling activity, which includes homo- or heterodimerization with IRAK1 or IRAK2 polypeptides, respectively, and interaction with TIR signaling polypeptides, such as Tollip, MyD88, and TRAF6; modulation of the mRNA levels, protein expression expression, or activities downstream effectors of IRAK1 in TIR signaling pathways, such as NF-κB and TRAF6; and modulation of the production of substances that are produced in a TIR signaling-dependent manner, such as TNFa and interleukin-6. Such modulation of IRAK1c activity can also derive from, or result in, covalent, ionic, of hydrophobic interactions between IRAK1c and other polypeptide, polysaccharide, lipid, fatty acid, small molecule, cation, anion, or metal moieties, thereby effecting a conformation change in IRAK1c resulting from such modulation. "Toll/IL-1 receptor" means a Toll-like receptor/IL-1 receptor family member, such as Toll-like receptor (TLR) 2, TLR3, TLR4, TLR5, TLR7, TLR9, the type I interleukin-1 receptor, the type II interleukin-1 receptor, the interleukin-12 receptor, and the interleukin-18 receptor.

Methods for detecting IRAK1c genomic DNA, cDNA, mRNA and expressed biologically active polypeptides are provided supra.

In addition, in a preferred exemplary embodiment, DNA microarrays commercially available may be used as platforms for the rapid comparison of IRAK1c expression levels between a test biological sample and the control sample. Such high throughput methods allow for the detection of altered gene expression on a global scale, and are thus useful in identifying gene expression profiles that are associated with Toll/interleukin-1 receptor signaling activity or IRAK1c activity associated medical conditions.

The Toll/interleukin-1 signaling cascade is a key mediator of inflammatory responses and activities; therefore, aberrations in this system can give rise to numerous medical conditions. Determining IRAK1c levels, whether absent, decrease, or increased relative to control levels in a test biological sample, can serve as a biomarker, or indicator, for such medical conditions. Exemplary such medical conditions include: pulmonary diseases and diseases of the airway, such as Adult Respiratory Disease Syndrome (ARDS), Chronic Obstructive Pulmonary Disease (OPD), pulmonary fibrosis, interstitial lung disease, lung adema, asthma, chronic cough, and allergic rhinitis; immunological disorders associated with transplantation; autoimmune diseases such as rheumatoid arthritis, systemic lupus erythematosus, multiple sclerosis, and diabetes (e.g., type I diabetes mellitus), HIV and AIDS; hyperproliferative disorders, such as cancer including solid tumors, skin cancers, and lymphomas; cardiovascular diseases including stroke, atherosclerosis, and tachycardia; diseases of the central nervous system including neurodegenerative diseases and disorders, such as neurogenic inflammation; non-CD14 mediated sepsis, CD14 mediated sepsis, and septic shock; osteoarthritis; osteoporosis; psoriasis and diseases of the skin, such as rash and contact and atopic dermatitis; inflammatory bowel disease such as Crohn's disease and ulcerative colitis; Behcet's syndrome; ankylosing spondylitis; sarcoidosis; gout; ophthalmic diseases and conditions; renal failure; and pain.

In various preferred embodiments, methods for the detection of IRAK1c mRNA and polypeptide levels (e.g., mRNA detection, identification, and quantitation techniques, and immunoassay-based polypeptide detection, identification and quantitation techniques) are employed for the detection or diagnosis of medical conditions mediated by modulation of Toll/interleukin-1 signaling activity.

In one embodiment, methods are provided to screen for compounds having IRAK1c-modulating activity comprising contacting an assay reagent comprising IRAK1c with a compound; measuring the activity of IRAK1c in the presence of the compound to produce a test activity measurement, and measuring the activity of IRAK1c in the absence of the compound to produce a control activity measurement; and comparing the test and control activity measurements, whereby a difference in such measurements identifies the compound as having IRAK1c-modulating activity.

An assay reagent can be, for example, one of the following: an isolated IRAK1c polypeptide, an isolated and substantially purified IRAK1c polypeptide, a cell comprising an IRAK1c polypeptide, a tissue specimen, a tissue biopsy, a bodily fluid, an organ specimen, a whole organism, or any other biological sample that comprises an IRAK1c polypeptide.

Compounds tested as modulators of an IRAK1c protein can be any small chemical compound, or a biological entity, such as a protein, sugar, nucleic acid or lipid. Alternatively, modulators can be genetically altered versions of an IRAK1c gene. Preferably, test compounds are small chemical molecules or peptides. Any suitable chemical compound can be tested as a potential modulator or binding compound in the assays of the invention, e.g., from a chemical library. Compounds can be dissolved in aqueous or organic (e.g., DMSO-based) solutions. The assays may be designed for high-throughput screening of large chemical libraries by automating the assay steps and assaying compounds in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In an example of a preferred embodiment, high throughput screening is performed by providing a combinatorial chemical or peptide library containing a large number of compounds having suitable pharmacophores. Such combinatorial chemical library compounds are then screened in assays according to the invention to identify those library members (particular chemical species or subclasses) that are potent IRAK1c modulators and display other desired characteristics. The modulators thus identified can serve as conventional "lead compounds" to arrive at IRAK1c-modulating compounds having optimized properties suitable as drug candidates or pharmaceuticals.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in various ways for a given compound length (i.e., the number of amino acids in a polypeptide compound). Myriad chemical compounds can be synthesized through such combinatorial mixing of chemical building blocks.

Techniques for the preparation and screening of combinatorial chemical libraries are known in the art. Such combinatorial chemical libraries include, peptide libraries (see, e.g., U.S. Pat. No. 5,010,175; Furka, *Int. J. Pept. Prot. Res.* 37:487-493 (1991); and Houghton et al., *Nature* 354:84-88 (1991)). Other chemistries for generating chemical diversity libraries can also be used. Such chemistries include the following: peptoids (e.g., WIPO Publication No. WO 91/19735), encoded peptides (e.g., WIPO Publication No. WO 93/20242), random bio-oligomers (e.g., WIPO Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), other small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger, and Sambrook, supra), peptide nucleic acid libraries (see, e.g., U.S. Pat. No. 5,539,083), antibody libraries (see, e.g., Vaughn et al., *Nature Biotechnology*, 14(3):309-314 (1996) and International Application No. PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum, *C&EN*, page 33 (Jan. 18, 1993); isoprenoids (U.S. Pat. No. 5,569,588); thiazolidinones and metathiazanones (U.S. Pat. No. 5,549,974); pyrrolidines (U.S. Pat. Nos. 5, 525,735 and 5,519,134); morpholino compounds (U.S. Pat. No. 5,506, 337); and benzodiazepines (U.S. Pat. No. 5,288,514).

Apparatus for the preparation of combinatorial libraries are commercially available (e.g., Advanced Chem Tech, Louisville, Ky.; Rainin, Woburn, Mass.; Applied Biosystems, Foster City, Calif.; Millipore, Bedford, Mass.). In addition, numerous combinatorial libraries are themselves commercially available.

In another exemplary embodiment, soluble assays may employ molecules such as an N-terminal or C-terminal domain either alone or covalently linked to a heterologous protein to create a chimeric molecule. In yet another exemplary embodiment, solid-phase based in vitro assays may be used in a high throughput format, where a IRAK1c domain, IRAK1c chimeric molecule, IRAK1c polypeptide, or cell or tissue expressing an IRAK1c polypeptide is attached to a solid-phase substrate.

In the high-throughput assays of the invention, it is possible to screen up to several thousand different potential modulators in a single day. In particular, each well of a microtiter plate can be used to run a separate assay against a selected test compound, or, if concentration or incubation time effects are to be observed, every 5-10 wells can test a single compound.

Thus, a single standard microtiter plate can assay about 100 (e.g., 96) compounds. If 1536-well plates are used, then a single plate can be used to assay from about 100 to about 1500 different compounds. Microfluidic approaches to reagent manipulation may also be employed.

The molecule of interest can be bound to the solid-state component, directly or indirectly, via covalent or non-covalent linkage, e.g., via a tag. The tag can be any of a variety of components. For example, a molecule that binds the tag (a tag binder) is fixed to a solid support, and the tagged molecule of interest is attached to the solid support by interaction of the tag and the tag binder.

A number of tags and tag binders can be used, based upon known molecular interactions described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin and appropriate tag binders are also commercially available).

Similarly, a suitable haptenic or antigenic compound can be used in combination with an appropriate antibody to form a tag/tag binder pair. Thousands of specific antibodies are commercially available and many additional antibodies are described in the literature. For example, in one exemplary configuration, the tag is a first antibody and the tag binder is a second antibody, which recognizes the first antibody.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein.

Common linkers such as peptides, polyethers, and the like can also serve as tags, and include polypeptide sequences, such as poly-gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent that fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996). Non-chemical approaches for fixing tag binders to substrates include other common methods, such as heat, cross-linking by UV radiation.

In a preferred embodiment, the comparison step comprises detecting an alteration in IRAK1c mRNA levels, IRAK1c protein levels, secreted interleukin-6 levels, secreted tumor necrosis factor alpha levels, association with IRAK1, association with IRAK2, association with Tollip, association with MyD88, or association with TRAF6.

Compounds that interact with biologically active IRAK1c proteins can be isolated based on an ability to specifically bind to an IRAK1c polypeptide. In exemplary embodiments, the IRAK1c may be attached to a solid support. In one embodiment, affinity columns are made using the IRAK1c polypeptide, and physically-interacting molecules are identified. In addition, molecules that interact with IRAK1c proteins in vivo can be identified by chromatographic techniques, co-immunoprecipitation or other methods, such as immunoprecipitating IRAK1c proteins using anti-IRAK1 or anti-IRAK1c antibodies from a cell or cell extract, and identifying compounds, e.g., proteins, that are precipitated along with the IRAK1c protein.

Two-hybrid screens can also be used to identify polypeptides that interact in vivo with an IRAK1c polypeptide (see Fields et al., *Nature* 340:245-246 (1989)). Such screens comprise two discrete, modular domains of a transcription factor protein, e.g., a DNA binding domain and a transcriptional activation domain, which are produced in a cell as two separate polypeptides, each of which also comprises one of two potentially binding polypeptides. If the two potentially binding polypeptides in fact interact in vivo, then the DNA binding and the transcriptional activating domain of the transcription factor are united, thereby producing expression of a target gene in the cell. The target gene generally encodes an easily detectable gene product, e.g., β-galactosidase, GFP, or luciferase, which can be detected using standard methods. In the present invention, an IRAK1c polypeptide is fused to one of the two domains of the transcription factor, and the potential IRAK1c-binding polypeptides (e.g., encoded by a cDNA library) are fused to the other domain using known techniques.

IPAK1c splice variants encode polypeptides that attenuate IL-1/Toll receptor signal transduction. Accordingly, the activity of IRAK1c polypeptides can be assessed using a variety of in vitro and in vivo assays to determine functional, chemical, and physical effects, e.g., directly measuring the expression or activity of downstream effectors such as NF-κB or TRAF6, measuring the binding of IRAK1c to heterologous proteins, e.g., TRAF6 or MyD88, or to other molecules (e.g., radioactive binding), measuring IRAK1c protein and/or RNA levels, or measuring other aspects of IRAK1c polypeptides, e.g., phosphorylation levels, transcription levels, and the like. Such assays can be used to test for both activators and inhibitors of IRAK1c proteins. Such modulators of activity are useful for various diagnostic and therapeutic applications.

In an illustrative embodiment, samples or assays that are treated with a potential IRAK1c protein modulator are compared to control samples without the test compound, to examine the extent of modulation. Control samples (untreated with modulators) are assigned a relative IRAK1c activity value of 100. Percent modulation of IRAK1c protein by the test compound relative to the control is measured to reflect its IRAK1c activity.

The effects of the test compounds on the function of IRAK1c polypeptides can be measured by examining any suitable physiological change that affects IRAK1c activity. When the functional consequences are determined using intact cells or animals, one can also measure a variety of effects such as changes in inflammation of tissues, as indicated by, e.g., pain, heat, redness, swelling, loss of function, dilatation of arterioles, capillaries and venules, with increased permeability and blood flow, exudation of fluids, including plasma proteins and leucocytic migration into the site of inflammation.

Alternatively, transcription levels can be measured to assess the effects of a test compound on IRAK1c signal transduction. A host cell containing an IRAK1c protein of interest may be contacted with a test compound for a sufficient time to effect any interactions, and then the level of gene expression can be measured. The amount of time to effect such interactions may be empirically determined, such as by running a time course and measuring the level of transcription as a function of time. The amount of transcription may be measured using any suitable known method. For example, mRNA expression of the protein of interest may be detected using Northern blots or by detecting their polypeptide products using immunoassays. A polynucleotide that is expressed following IRAK1c activation can be used, e.g., any gene with an NF-κB cognate DNA binding site (see, e.g., Lenardo et al., Cell 58:227 (1989); Grilli et al., Int. Rev. Cytol. 143:1 (1993); Baeuerle et al., Ann. Rev. Immunol. 12:141 (1994)). Such assays can use natural targets of NF-κB or can use reporter genes, e.g., chloramphenicol acetyltransferase, luciferase, β-galactosidase, GFP, and alkaline phosphatase, operably linked to a promoter containing an NF-κB binding site. Furthermore, the protein of interest can be used as an indirect reporter via attachment to a second reporter such as green fluorescent protein (see, e.g., Mistili & Spector, Nature Biotechnology 15:961-964 (1997)).

The amount of transcription may then be compared to the amount of transcription in either the same cell in the absence of the test compound. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

In still another preferred embodiment, the test compound is a component of a solution. The solution can be an aqueous solution or a non-aqueous solution, and can comprise, in addition to a solvent (e.g., polar or non-polar), a pH buffer, a salt, and can exist as an electrolytic solution, a suspension, a colloid, a paste, a gel, a polymer, a co-polymer, a block polymer, or any suitable combination thereof. In yet another preferred embodiment, the test compound is part of a composition comprising a buffer.

In certain embodiments or the present invention, methods are provided for treating a medical condition mediated by modulation of Toll/interleukin-1 receptor signaling activity or IRAK1 activity, comprising administering to a subject in need thereof a therapeutically effective amount of a compound identified as having IRAK1c-modulating activity.

The term "treating" includes preventing, decreasing, diminishing, suppressing, alleviating, or ameliorating the symptoms or causes of a medical condition. Such treatment can be therapeutic or prophylactic.

The term "subject" as used herein refers to an animal who is the object of treatment, observation or experiment. Preferably, the subject is a mammal, more preferably a human.

A "pharmaceutically effective amount" is an amount or dose sufficient to achieve the desired IRAK1c-modulating effect. Suitable amounts for a particular treatment may be ascertained by routine methods such as modeling, dose escalation studies or clinical trials, and by taking into consideration routine factors, e.g., the mode or route of administration or drug delivery, the pharmacokinetics of the agent, the severity and course of the disorder or condition, the subject's previous or ongoing therapy, the subject's health status and response to drugs, and the judgment of the treating physician. An exemplary dose is in the range of from about 0.001 to about 200 mg per kg of subject's body weight per day, preferably about 0.05 to 100 mg/kg/day, or about 1 to 35 mg/kg/day, in single or divided dosage units (e.g., BID, TID, QID). For a 70-kg human, an illustrative dosage amount is from about 0.05 to about 7 g/day, or about 0.2 to about 2.5 g/day.

Once improvement of the patient's conditions has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

The compounds or treatment agents of the invention may be used alone or in combination with one or more other active ingredients, to formulate pharmaceutical compositions of the invention. A pharmaceutical composition of the invention comprises a pharmaceutically effective amount of a compound having IRAK1c-modulating activity, which can be determined using methods as described above. A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils and polyethylene glycols.

Delivery forms of the pharmaceutical compositions containing one or more dosage units of the pharmaceutical agents may be prepared using suitable pharmaceutical excipients and compounding techniques known to those skilled in the art. The compositions may be administered in the inventive methods by oral, parenteral, rectal, topical, or ocular routes or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient mixed with pharmaceutically acceptable excipients such as inert diluents, disintegrating agents, binding agents, lubricating agents, sweetening agents, flavoring agents, coloring agents and preservatives agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol or water; preservatives (for example, methyl or propyl p-hydroxybenzoate or sorbic acid); wetting agents such as lecithin; and, if desired, flavoring or coloring agents.

The compositions of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Another embodiment of the invention provides a method for treating a medical condition comprising administering a pharmaceutically acceptable composition comprising a pharmaceutically acceptable vector of the invention.

IRAK1c nucleic acid molecules may be introduced into a cell, in vitro, in vivo, or ex vivo, using any suitable method, e.g., infection with viral vectors, liposome-based methods, biolistic particle acceleration, and naked DNA injection. Such therapeutically useful nucleic acids include coding sequences for biologically active dominant negative IRAK1c. Such a sequence may be operably linked to a promoter as described above. The nucleic acid may be administered in the form of a cell that is itself directly therapeutically effective, e.g., certain antisense or ribozyme molecules. These antisense molecules may be DNA, stable derivatives of DNA such as phosphorothioates or methylphosphonates, RNA, stable derivatives of RNA such as 2'-O-alkylRNA, or other IRAK1c antisense oligonucleotide mimetics. IRAK1c antisense molecules may be introduced into cells by microinjection, liposome encapsulation or by expression from vectors harboring the antisense sequence.

IRAK1c gene therapy may be used to introduce IRAK1c into the cells of target organisms. To illustrate, the IRAK1c DNA is ligated into viral vectors that mediate transfer of the IRAK1c DNA by infection of recipient host cells. Suitable exemplary viral vectors include retrovirus, adenovirus, adeno-associated virus, herpes virus, vaccinia virus, poliovirus and the like. Alternatively, IRAK1c DNA can be transferred into cells for gene therapy by non-viral techniques, such as receptor-mediated targeted DNA transfer using ligand-DNA conjugates or adenovirus-ligand-DNA conjugates, lipofection membrane fusion, or direct microinjection. Protocols for molecular methodology of gene therapy suitable for use with the IRAK1c gene are exemplified in GENE THERAPY PROTOCOLS, edited by Paul D. Robbins, Human press, Totawa N.J., 1996.

Pharmaceutically effective compositions comprising IRAK1c DNA, IRAK1c RNA, or IRAK1c polypeptides, or modulators of IRAK1c activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the polypeptide, DNA, RNA, or modulator.

Other exemplary and preferred embodiments of the invention will be apparent from the following examples.

EXAMPLE 1

Cloning, In Vivo Expression Profile, and Recombinant Expression of Human IRAK1c

This example describes the cloning, in vivo expression profile, and recombinant expression of human IRAK1c.

In the course of studying the expression of IRAK1 in human cell lines and tissues, the IRAK1c splice variant was cloned from a human spleen cDNA library. Sequence analyses indicated that this splice variant lacks the complete 237 bp comprising exon 11 of IRAK1, which encodes amino acids 435-514 of the full length human IRAK1 protein (FIG. 1A). IRAK1c was subsequently cloned and sequence verified from human peripheral blood mononuclear cells as well as Jurkat and HeLa cell cDNA libraries using Superscript II (Invitrogen). cDNA for the IRAK1c splice variant was amplified using the GC-rich PCRx system (Invitrogen) according to the manufacturer's instructions.

Figure 1B:
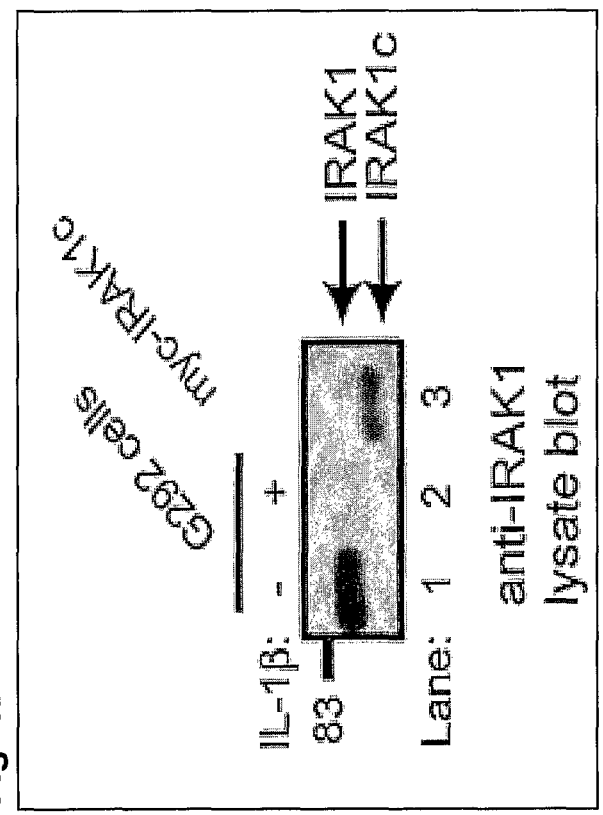

To further characterize the IRAK1c splice variant, human embryonic kidney cells (293T, ATCC #CRL-11268) maintained in Dulbecco's modified Eagle's medium containing 10% fetal calf serum, 20 mM HEPES, 1 mM sodium pyruvate, 1 mM nonessential amino acids, 100 U of penicillin per ml, and 100 U of streptomycin per ml (Hyclone) were transfected with 0.5 µg of the pCDNA3.1-myc-IRAK1c expression vector. Also, human osteosarcoma cells (G292, ATCC #CRL-1423) which express endogenous IRAK1, were maintained in McCoy's medium containing 10% fetal calf serum and penicillin/streptomycin (HyClone) and either stimulated with interleukin 1-beta (Il-1β, R&D Systems)or left unstimulated. 48 hours following transfection and stimulation, the 293T cells and G292 cells were lysed in a Triton-containing lysis buffer (0.5% Triton X-100, 50 mM Tris pH7.5, 150 mM NaCl, 1 mM NaF, 1 mM $Na_3VO_4$, 20 µM aprotinin, 1 mM PMSF) followed by immunoblot analysis of prepared lysates using an anti-IRAK1 rabbit polyclonal antibody (Santa Cruz Biotechnology). The results revealed that while the Il-1β-stimulated G292 cells expressed the full length IRAK1 protein, as expected, the 293T cells transfected with the IRAK1c splice variant expressed an anti-IPAK1 antibody-reacting protein of approximately 68 kDa (FIG. 1B).

In order to further characterize the expression profiles of IRAK1 and the IRAK1c splice variant, respectively, the reverse transcriptase (RT)-PCR forward primers set forth in FIG. 2, SEQ ID NO: 1, 5' GAC CAA GTA TCT GAA AGA CCT GGT G 3', which specifically anneals to IRAK1 transcripts, and SEQ ID NO: 2, 5' GAC CAA GTA TCT GGT GTA CGA GAG 3', which specifically anneals to IRAK1c transcripts, were designed. The IRAK1-specific forward primer, SEQ ID NO: 1, spans the junction of exon 10 and exon 11 in order to facilitate specific amplification of IRAK1; the IRAK1c-specific forward primer, SEQ ID NO: 2, spans the junction of exon 10 and 12, and thus facilitates specific amplification of IRAK1c. Both forward primers were used with a common IRAK1 reverse primer, SEQ ID NO: 3, 5' TCA GCT CTG AAA TTC ATC ACT TTC 3'. Control amplification primers for glyceraldehyde-3-phosphate dehydrogenase (GAPDH) were from Promega. PCR products were separated on agarose gels and visualized after ethidium-bromide staining in accordance with standard, art-recognized methods. These primers were validated using cDNA from cells transfected with IRAK1 or IRAK1c expression vectors.

Figure 1C:
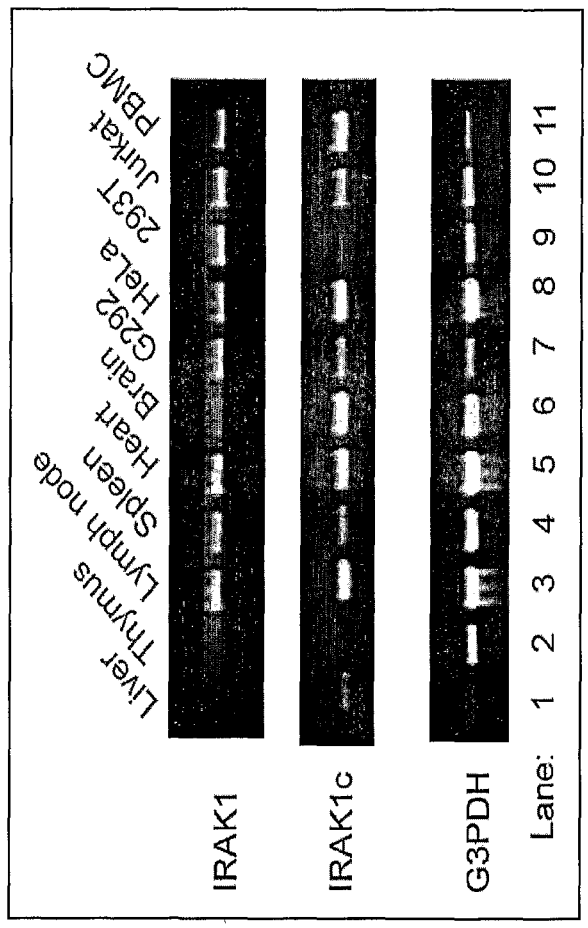

Using these primers, the expression profiles of IRAK1c and IRAK1 were characterized by RTPCR using RNA from human liver, thymus, lymph node, spleen, heart, and brain (all from BD Biosciences), as well G292 cells, HeLa cells (ATCC #CCL-2), 293T cells, Jurkat cells (ATCC #TIB-152), and human peripheral blood mononuclear (PMBC) cells (FIG. 1C). G292 and 293T cells were maintained as described above. PMBC cells were purified to 99% purity from peripheral human blood using CD14 microbeads and separated on an Auto Macs (Miltenyi Biotech). The results showed that both IRAK1 and IRAK1c were widely expressed in many of the tissues and cell lines tested; however, when compared to wild type IRAK1, IRAK1c was more abundantly expressed in brain and the liver (FIG. 1C).

To confirm the IRAK1c RTPCR results at the protein level, lysates obtained from human brain and liver, as well as from the human moncoytic cell line THP-1 (ATCC #TIB-202) and myc-IRAK1c-transfected 293T cells, were analyzed. THP-1 cells were maintained in endotoxin free RPMI (Sigma) containing 10% endotoxin free fetal calf serum (Invitrogen) and endotoxin free penicillin/streptomycin (Sigma) Cells were lysed as described above, and the lysates clarified by centrifugation at 14,000×g for 10 min at 4° C. Total protein extracts from each sample were incubated with 5 µg of antibody for 2 h, followed by a 1 h incubation with 20 µl of protein G-Sepharose beads (Amersham Biosciences). After incubation, the beads were washed four times with lysis buffer, separated by sodium dodecyl sulfate-polyacrylamide gel electrophoresis (SDS-PAGE), transferred to Immobilon-P membranes (Millipore), and analyzed by immunoblotting as previously described (Rao et al., 2002, *Signal Transduction* 2:29-39).

Figure 1D:
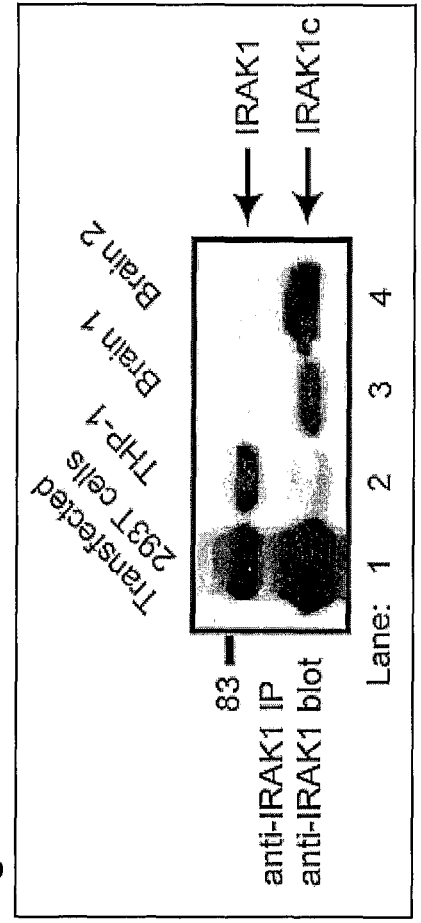

The results show that compared to 293T cells transfected with IRAK1c, lysates prepared from whole brain showed preferential expression of IRAK1c compared to IRAK1 (FIG. 1D). A lower level of IRAK1c expression was seen in liver as well as the THP-1 cell line. Taken together, these results indicated that IRAK1c is an alternatively spliced variant of IRAK1 that is expressed in several tissues, but preferentially expressed in brain and liver.

Using similar methods, IRAK1c from other animals, such as, but not limited to, rat, mouse, horse, dog, and pig, can be similarly cloned and recombinantly expressed by means provided herein as well as by those means know to the skilled artisan.

EXAMPLE 2

Characterization of IRAK1c Kinase Activity

This example describes the direct determination in vitro of any kinase activity of the human IRAK1c splice variant in comparison to that observed for human IRAK1.

Kinase dead myc-IRAK1 (myc-IRAK-KD) and myc-IRAK1c (myc-IRAK1c-KD)-containing pCDNA3.1 expression vectors were generated by site-directed mutagenesis. The forward and reverse primers, SEQ ID NO: 4 and SEQ ID NO: 5 (FIG. 2A), were used to introduce a point mutation in each respective clone that created a lysine to alanine substitution at amino acid position 239 (K239A). This amino acid position had previously been determined to be important for the catalytic activity of wild-type IRAK1.

The pCDNA3.1 expression vectors comprising Myc-IRAK1, myc-IRAK1c, myc-IRAK1-KD, and IRAK1c-KD, prepared as described above, or empty pCDNA3.1 expression vector were transfected into 293T cells. Cells were then lysed and immunoprecipitated with the anti-myc tag antibody (Covance) in kinase lysis buffer (50 mM HEPES pH 7.9, 20 mM $MgCl_2$, 1% TX-100, 1 mM NaF, 1 mM $Na_3VO_4$, 20 mM gylcerol-2-phosphate, 5 mM p-nitrophenyl-phosphate, 1 mM DTT, 1 mM PMSF). Immunoprecipitates were incubated in kinase buffer (20 mM Tris pH 7.5, 20 mM $MgCl_2$, 1 mM EDTA, 1 mM $Na_3VO_4$, 20 mM gylcerol-2-phosphate, 20 mM p-nitrophenyl-phosphate, 500 nM IRAK4, 1 mM DTT, 2 pg MBP substrate, 20 µM ATP and 10 µCi $\gamma^{32}$-P-ATP) for 20 min at 32° C. Reactions were stopped by the addition of 3× SDS-PAGE sample buffer. Samples were subjected to SDS-PAGE, transferred to Immobilon-P membranes and the proteins were visualized and quantified by autoradiography using a Typhoon 8600 Variable Mode Imager (Amersham Biosciences).

Figure 3B:
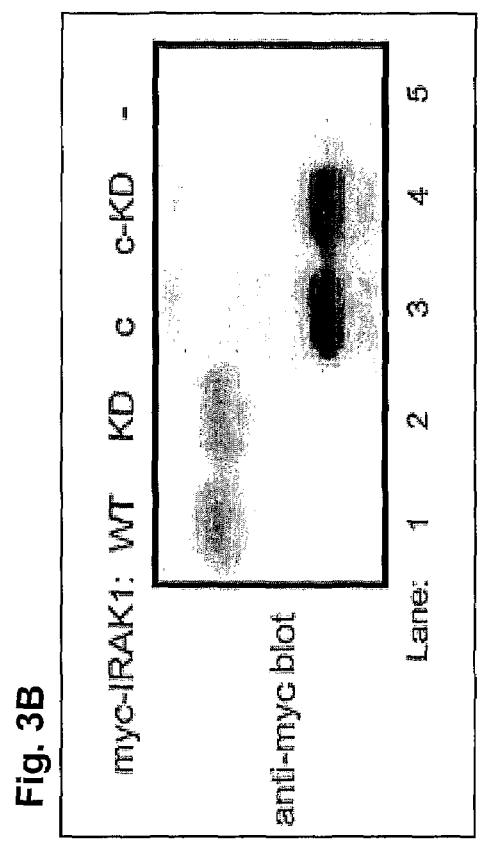
FIGS. 3A and 3B demonstrate that the IRAK1c variant is a kinase-dead variant of IRAK1.
Figure 3A:
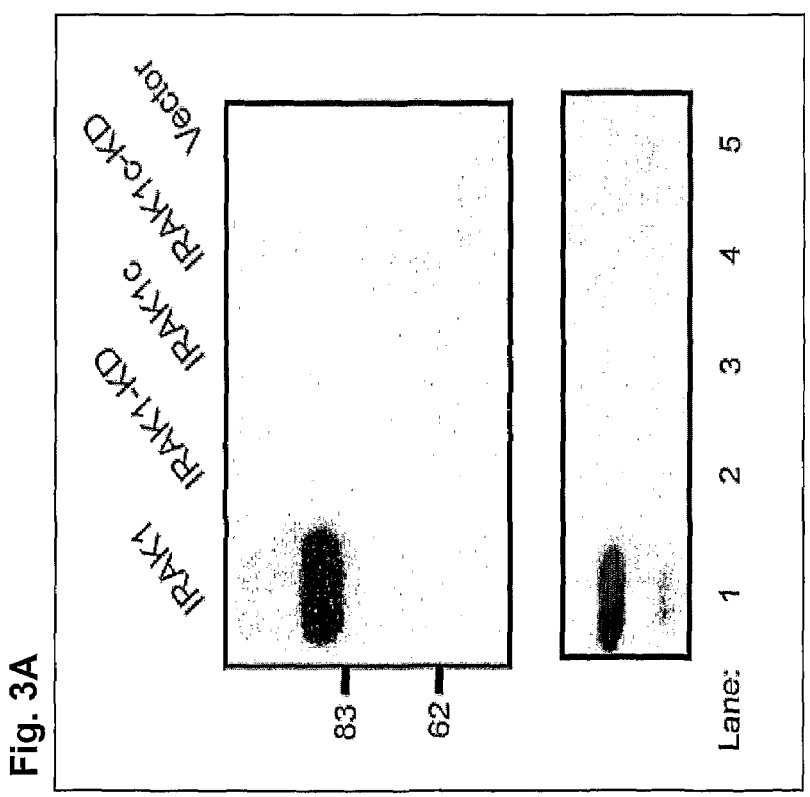

The results show that IRAK1 expressed in 293T cells was constitutively active, as seen by autophosphorylation as well as phosphorylation of a myelin basic protein substrate (FIG. 3A, lane 1). In contrast, IRAK1c showed no kinase activity, and behaved like the IRAK1-KD point mutant, K239S, that rendered the IRAK1 protein kinase inactive. These data indicated that the amino acids encoded by exon 11, which are absent in IRAK1c, are required for kinase activity. Anti-myc western immunoblotting confirmed that all myc-IRAK1 proteins were efficiently expressed and immunoprecipitated in this assay (FIG. 3B).

Using similar methods, the kinase activity of endogenous and recombinant IRAK1 and IPAK1c derived from other animal tissues, such as, but not limited to, rat, mouse, horse, dog, and pig, by means set forth herein as well as be means well known by the skilled artisan, can be performed.

EXAMPLE 3

Characterization of the Functional Consequence of the Lack of Kinase Activity for IRAK1c The lack of IRAK1c kinase activity suggested that this splice variant might serve as a regulator of TIR family signaling. To explore this possibility, a firefly luciferase reporter gene assay was performed using the pHTS-NF-κB luciferase plasmid (Biomyx Technology) to assay for NF-κB activation upon stimulation with IL-1β (R&D Systems) in the presence or absence of transfected myc-IRAK1 expression vectors (described above). The pHTS-NF-κB luciferase plasmid contains five tandemerized NE-κB concensus response elements operably linked to a Herpes Simplex Virus-Thymidine Kinase (HSV-TK) promoter, which when bound by activated NF-κB, drive efficient transcription of the luciferase reporter gene and, ultimately, high levels of active luciferase enzyme relative to baseline levels. The level of luciferase activity is quantitated by measuring the amount of light emitted at approximately 560 nanometers (nm) when a sample of the lysate from transfected cells is incubated with luciferin (the substrate for luciferase) in an appropriate assay buffer; the luciferin is hydrolyzed by the luciferase and a concomitant quantity of light is emitted. Therefore, in this system, the relative amount of light emitted from lysates of transfected cells is a linear function of the level of NF-κB activity elicited by the conditions of the transfection.

Figure 4B:
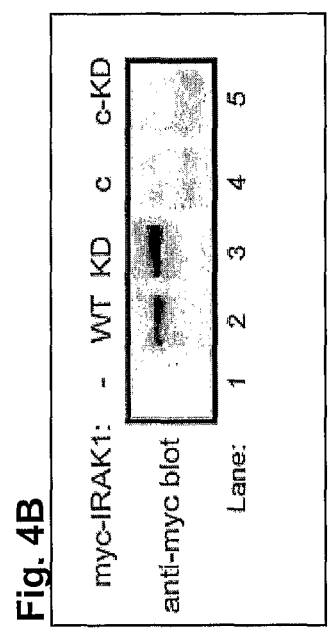
FIGS. 4A-4G demonstrate blockage of NF-$_k$B activity in 293T and G292 cells.
Figure 4D:
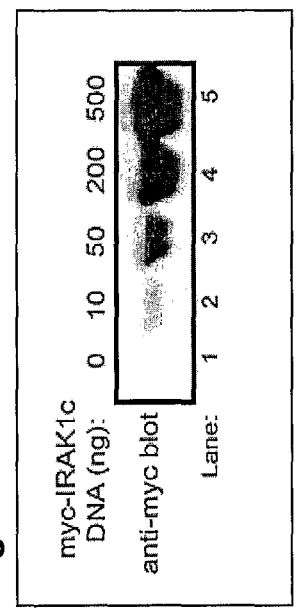
Figure 4A:
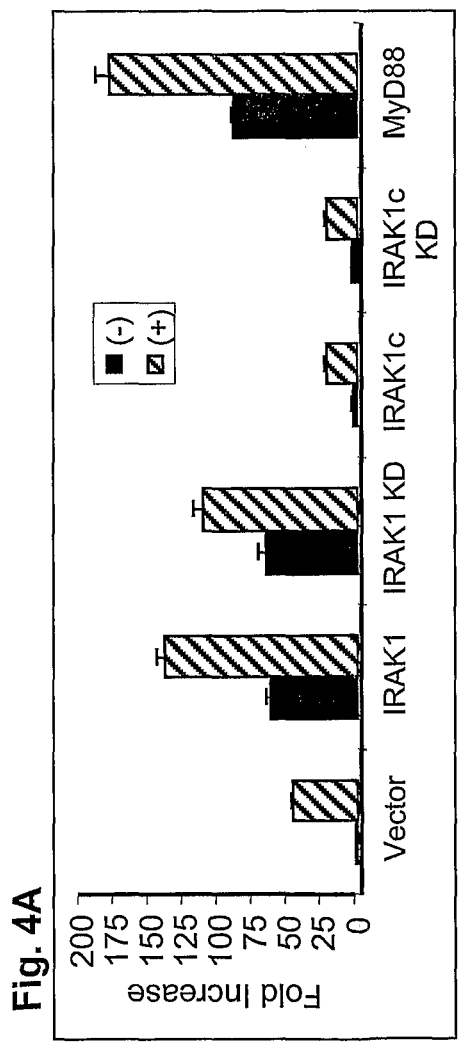
Figure 4C:
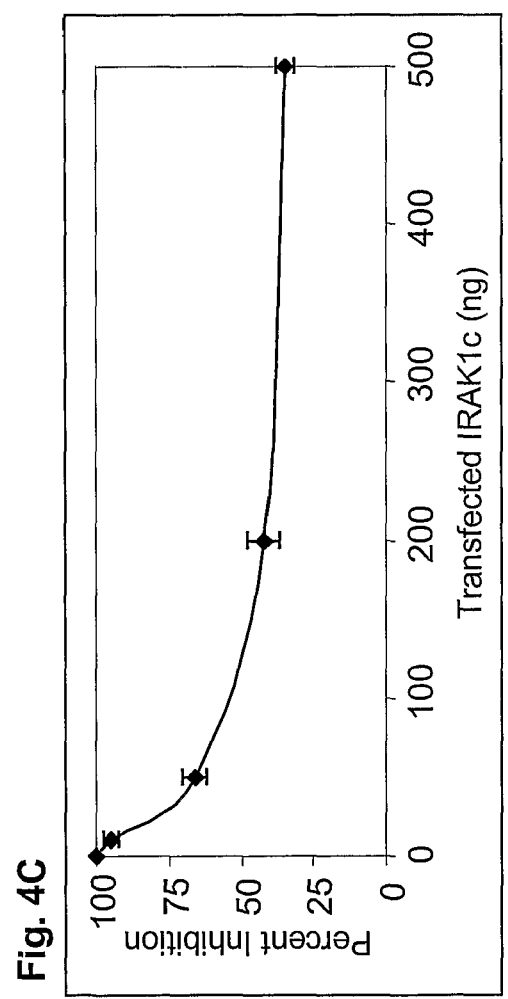

293T cells were seeded in 24-well plates and transiently transfected with 1 μg the pHTS-NF-κB luciferase reporter plasmid and 250 ng of either one of the myc-IRAK1 expression vectors using the Fugene-6 (Roche) transfection agent. Cells transfected with ten-fold less pCDNA3.1-myc-MyD88 expression vector along with the PHTS-NF-κB luciferase reporter were used as a positive control. After transfection, the cells were stimulated with 5 ng/ml IL-1β for 12 hours, then lysed in Glo lysis buffer (Promega) and analyzed for luciferase activity using the Bright Glo Luciferase assay system (Promega). Transfection of the MyD88 expression vector resulted resulting in high levels of NF-κB activation, even in the absence of IL-1β stimulation (FIG. 4A). As previously reported (Li et al., 2001, *Proceedings of the National Academy of Sciences USA* 98:4461-4465), both IRAK1 and IRAK1-KD activated NFκB-luciferase reporter activity in transfected 293T cells upon IL-1β stimulation (FIG. 4A). However, the kinase dead splice variant IRAK1c potently inhibited NFκB activation; furthermore, this negative effect of IRAK1c was dose dependent (FIG. 4C).

Figure 4E:
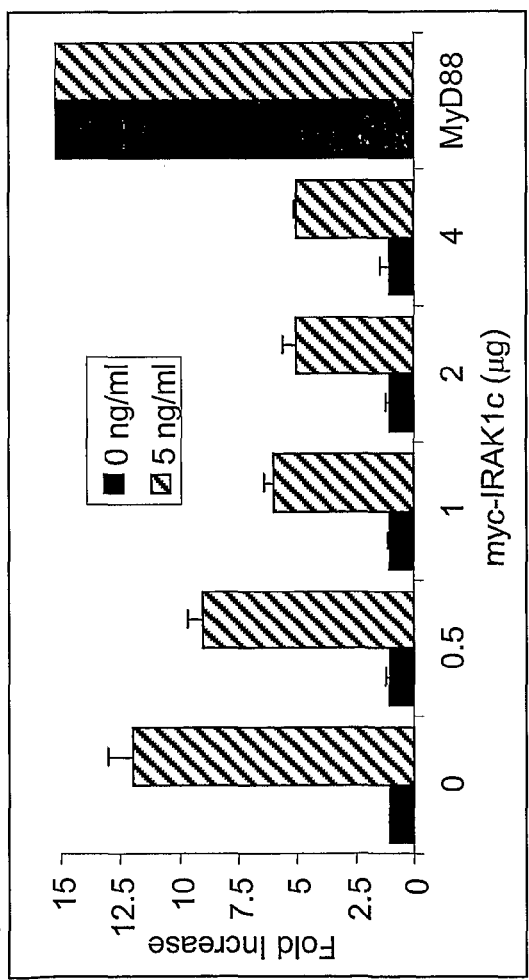
Figure 4F:
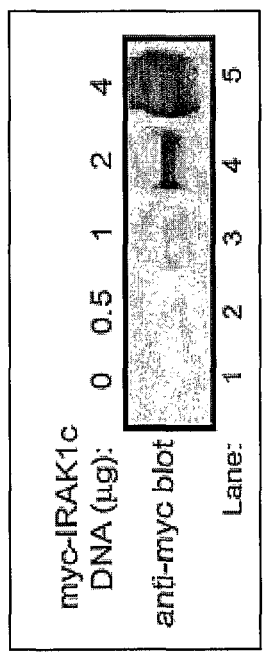

To ensure that these observed effects were not cell line specific, a similar experiment was performed using the IL-1-responsive G292 cell line, using the indicated amounts of myc-IRAK1c (FIG. 4E). In this experimental system, IRAK1c also functioned as a potent negative regulator that blocked IL-1β-induced NFκB activation in a dose dependent manner. Western immunoblot analyses of extracts in each of these experiments confirmed expression of the transfected constructs (FIGS. 4B, 4D, and 4F).

Figure 4G:
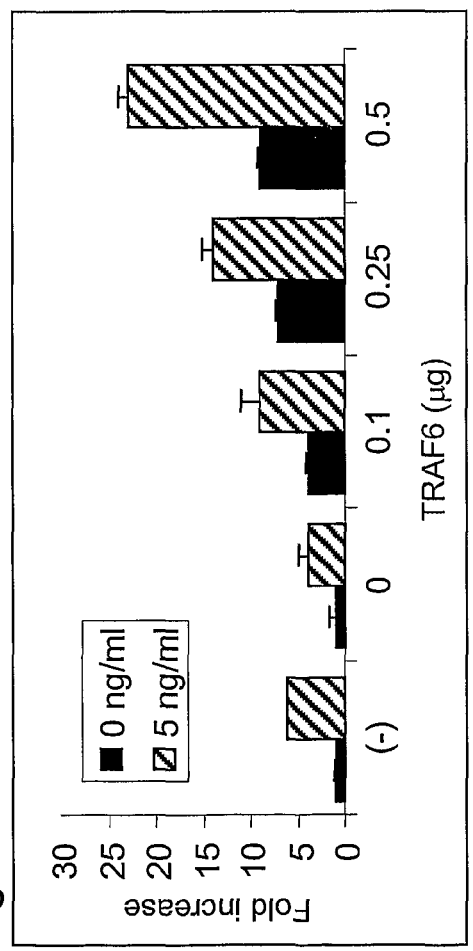

In order to determine if IRAK1c block activation of the downstream effector TRAF6, G292 cells were co-transfected with 250 ng myc-IRAK1c and the indicated amounts of pCDNA3.1-myc-TRAF6 (FIG. 4G). The results show that overexpression of myc-TRAF6 attenuated the inhibitory effect of IRAK1c on NFκB activation in a dose-dependent manner.

EXAMPLE 4

Inhibition of Pro-Inflammatory Cytokine Production as a Result of IRAK1c Expression Retroviral vectors were prepared by cloning myc-IRAK1, myc-IRAK1-KD, myc-IRAK1c, or HA-IRAK1c coding sequences into Ms cvPuro (BD Biosciences), and retrovirus was produced in the provided 293 packaging cell line. Stable transfectants of G292 and THP-1 cells were derived by continuous selection in puromycin (Sigma), with tagged protein expression verified by immunoblotting and intracellular staining.

Figure 5A:
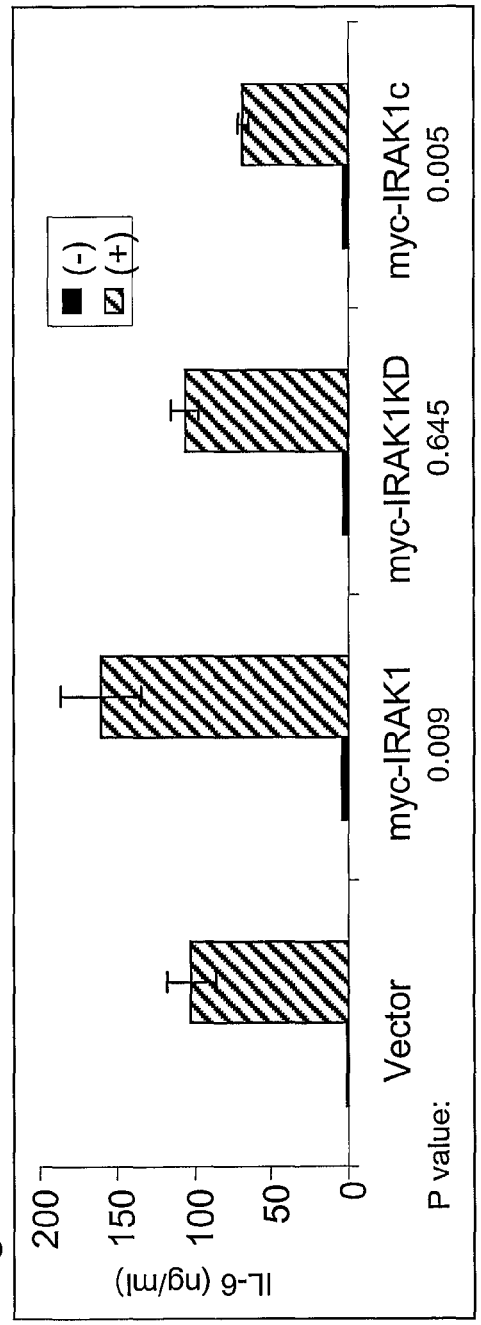
FIGS. 5A and 5B depict the inhibition of IL-6 and TNFa secretion by IRAK1c expression in LPS-stimulated THP-1 cells.

Stably transduced THP-1 cells ($1 \times 10^4$/well) expressing the indicated myc-IRAK1 constructs were incubated overnight in 96 well plates, stimulated for 12 hr with 50 ng/ml lipopolysaccharide (LPS, Sigma), and then tested for the ability to produce the for-inflammatory cytokine interleukin-6 (IL-6). Supernatants were analyzed for secreted IL-6 levels using Enzyme-Linked Immunosorbent Assay (ELISA) kits (R&D Systems). Overexpression of myc-IRAK1 resulted in an increase of IL-6 production that was statistically significant (FIG. 5). As suggested by the NFκB-luciferase assays in EXAMPLE 3, IRAK1c functioned as an inhibitor that significantly decreased IL-6 production when compared to empty vector-transduced cells (statistical significance=p<0.005, calculated using Student's t test).

Figure 5B:
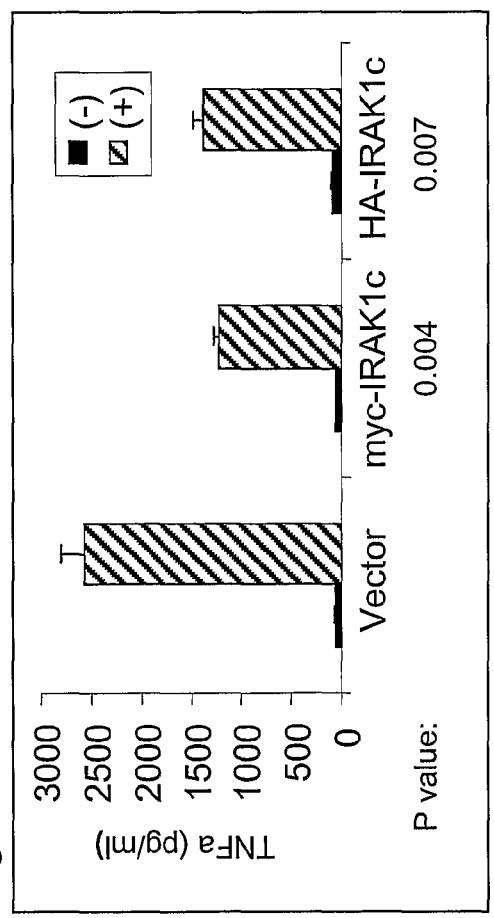

Since IRAK1 functions as a signaling molecule downstream of all TIR family members, stably-transduced cell lines using THP-1 monocytic cells. In this system, the ability of IRAK1c to regulate Toll like receptor-4 signaling was tested. Upon LPS treatment, THP-1 cells secrete the inflammatory mediator TNFα (FIG. 5B); TNFA production significantly decreased in THP-1 cells that overexpressed myc-IRAK1c (significance calculated by Student's t test; p values are indicated). This effect was also observed in THP-1 cells overexpressing a HA-tagged or untagged IRAK1c. Similar results were obtained when THP-1 cells were stimulated with the Toll like receptor 9 ligand, CpG. These data indicated that the IRAK1c splice variant not only blocked NF-κB activation, but that it also significantly decreased production of inflammatory cytokines like TNFα and IL-6 upon activation of several TIR family members.

EXAMPLE 5

Analysis of Homo- and Hetero- Dimerization of IRAK1c with Other IRAK Proteins

Previous studies have demonstrated that IRAK1 forms homodimers as well as heterodimers with IRAK2 and IRAKM (Wesche et al., 1999, *Journal of Biological Chemistry* 274:19403-19410). It has been hypothesized that one mechanism by which IRAKM functions as a negative regulator is to bind IRAK1 and prevent phosphorylation by IRAK4 or disassociation from the receptor (Kobayashi et al., 2002, *Cell* 110:191-202). In order to determine whether IRAK1c could potentially function via this mechanism, IRAK1c was tested for the ability to form a homodimer with IRAK1 or a heterodimer with IRAK2.

Figure 6:
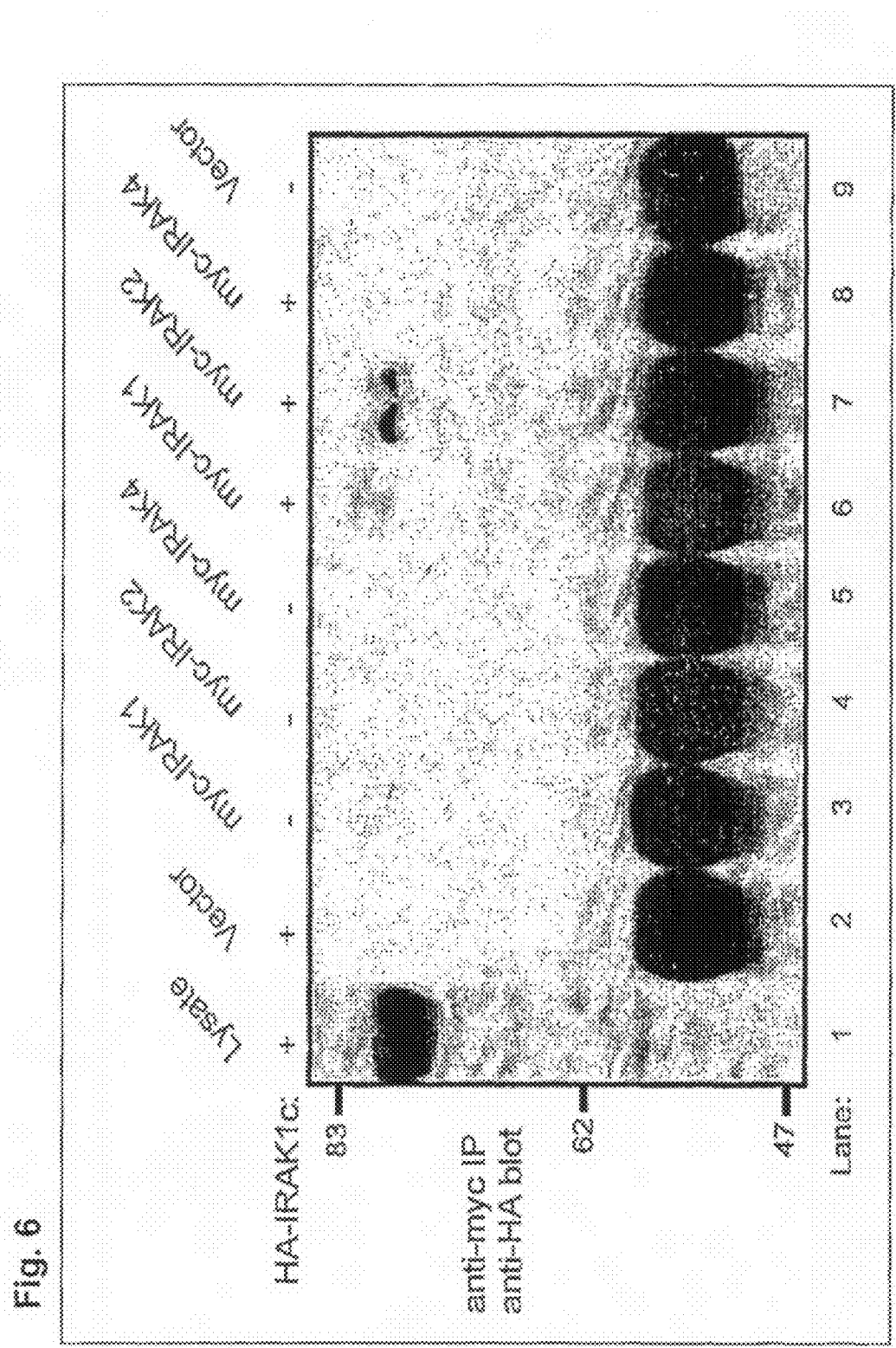
FIG. 6 illustrates IRAK1-IRAK1c and IRAK2-IRAK1c dimer formation in 293T cells transfected with the indicated myc-tagged plasmids and HA-IRAK1c or an empty vector control. Lysates prepared 48 hour ("hr") post-transfection were subjected to anti-myc immunoprecipitation followed by anti-HA immunoblot analysis.

293T cells were co-transfected with 1 μg HA-tagged IRAK1c and either of the myc-IHAK vectors or empty myc-vector as indicated in FIG. 6. Immunoblot analyses of complexes co-immunoprecipitated from cells lysed 48 hours post-transfection were performed as described above, using the anti-myc (Covance) antibody for the IP and the anti-HA tag antibody to immunoblot the SDS-PAGE-resolved immunoprecipitates. The results revealed that IRAK1c formed homodimers with IRAK1, as well as heterodimers with IPAK2 (FIG. 6).

EXAMPLE 6

Analysis of IRAK1c Association with TIR Family Signaling Proteins

In TIR signaling, IRAK1 is pre-associated with Tollip in the cytosol. Activation of TIRs recruits the IRAK1-Tollip complex to the receptor resulting in association with the MyD88 adaptor protein. This multimeric-signaling complex with IRAK1 also includes Pellino1 and Pellino2. IRAK1 also associates with TRAF6, a key signaling molecule in this pathway that activates JNK and NF-κB. The ability of IRAK1c to suppress activation signals downstream of TIR family members prompted the examination of any biochemical differences in the association with other signaling proteins in the TIR signaling pathway.

Figure 7:
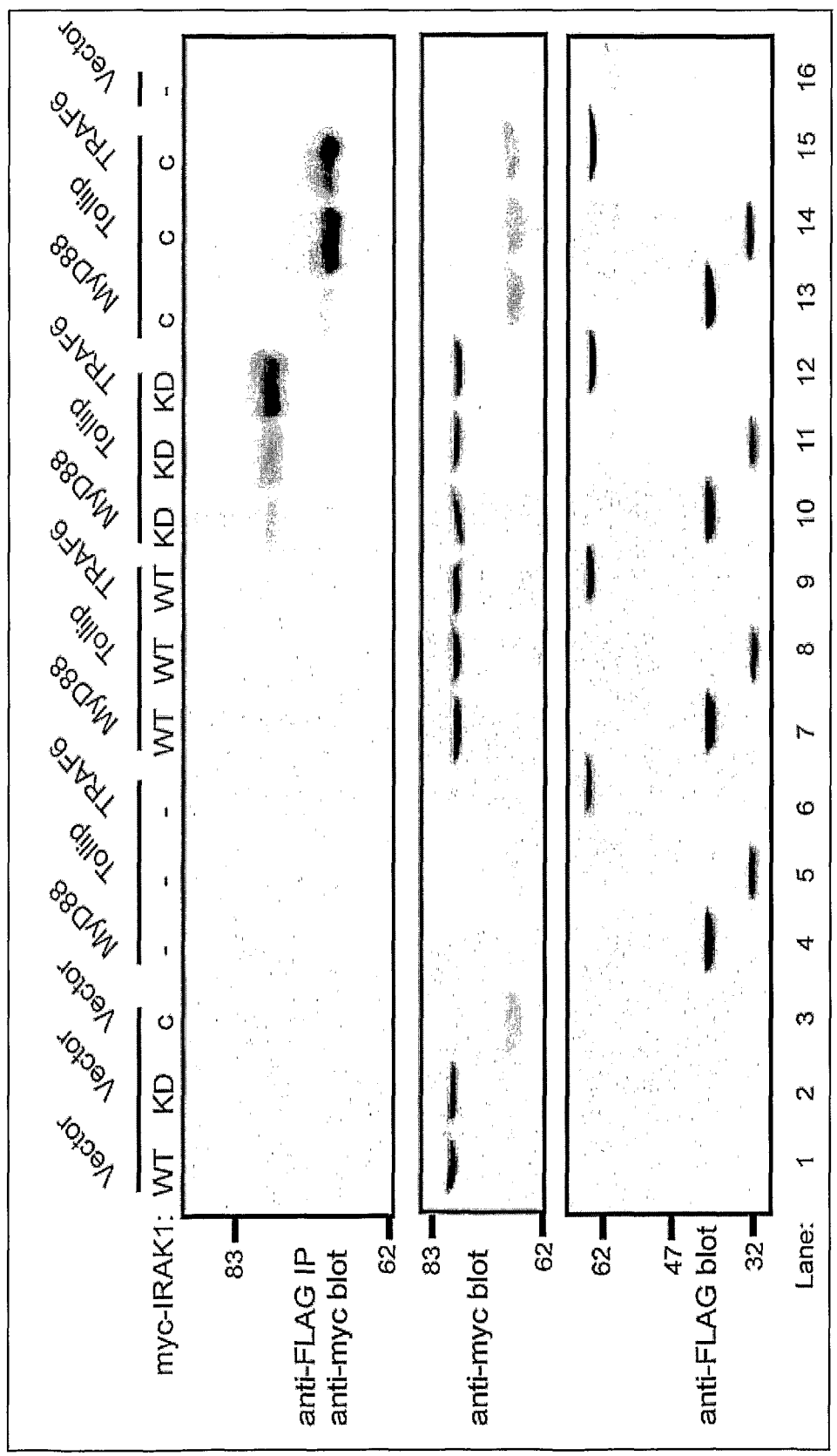
FIG. 7 illustrates the association of IRAK1c with MyD88, Tollip, and TRAF6 in 293T cells transfected with the indicated FLAG-tagged plasmids and the indicated myc-tagged IRAK1 plasmids. Lysates prepared 48 hr post-transfection were subjected to anti-FLAG immunoprecipitation followed by anti-myc immunoblot analysis. Whole cell lysates were also immunoblotted with anti-myc and anti-FLAG antibodies to confirm protein expression.

The indicated myc-tagged IRAK1 expression vectors (1 μg) were co-transfected either alone or with 1 μg of FLAG-tagged MyD88, Tollip, or TRAF6 in 293T cells. Transfected cells were lysed 48 hours post-transfection, FLAG-tagged proteins were immunoprecipitated using an anti-FLAG antibody (Sigma), separated by SDS-PAGE and immunoblotted with anti-myc antibody to detect co-immunoprecipitated IRAK1 proteins, as described above (FIG. 7). As previously reported, the kinase dead IRAK1 (myc-IRAK1-KD) associated more strongly with adaptor proteins in this pathway compared to IRAK1. Additionally, myc-IRAK1c strongly associated with MyD88, Tollip and TRAF6. Compared to the point mutation kinase dead IRAK1, the IRAK1c association with Tollip was more robust. Tollip is the adaptor protein that is pre-associated with IRAK1 and is responsible for recruiting IRAK1 from the cytosol to the receptor (Burns et al., 2000, *Nature Cell Biology* 2:346-251). The ability of IRAK1c to strongly associate with Tollip reflects IRAK1c recruitment to the receptor complex upon ligand activation.

EXAMPLE 7

Analysis of the Ability of IRAK1c to Serve as a Substrate for IRAK4-Mediated Phosphorylation Upon TIR activation, IRAK1 becomes phosphorylated on multiple residues resulting in a pronounced change in molecular weight in immunoblot analyses. IRAK4 is required to initiate the inflammatory response upon TIR activation, and has been shown to phosphorylate IRAK1 (Suzuki et al., 2002, *Nature,* 416:750-756; Li et al., 2002 *Proceedings of the National Academy of Sciences USA* 99:5567-5572). Kollewe et al. have demonstrated that IRAK1 is activated in a sequential manner (Kollewe et al., 2004, *Journal of Biological Chemistry* 279:5227-5236). First, IRAK4 phosphorylates Thr$^{209}$ resulting in a conformational change in the kinase domain. This results in phosphorylation of Thr$^{387}$ in the activation loop. IRAK1 then becomes autophosphorylated on several residues in the ProST region located between the death domain and kinase domain.

Figure 8:
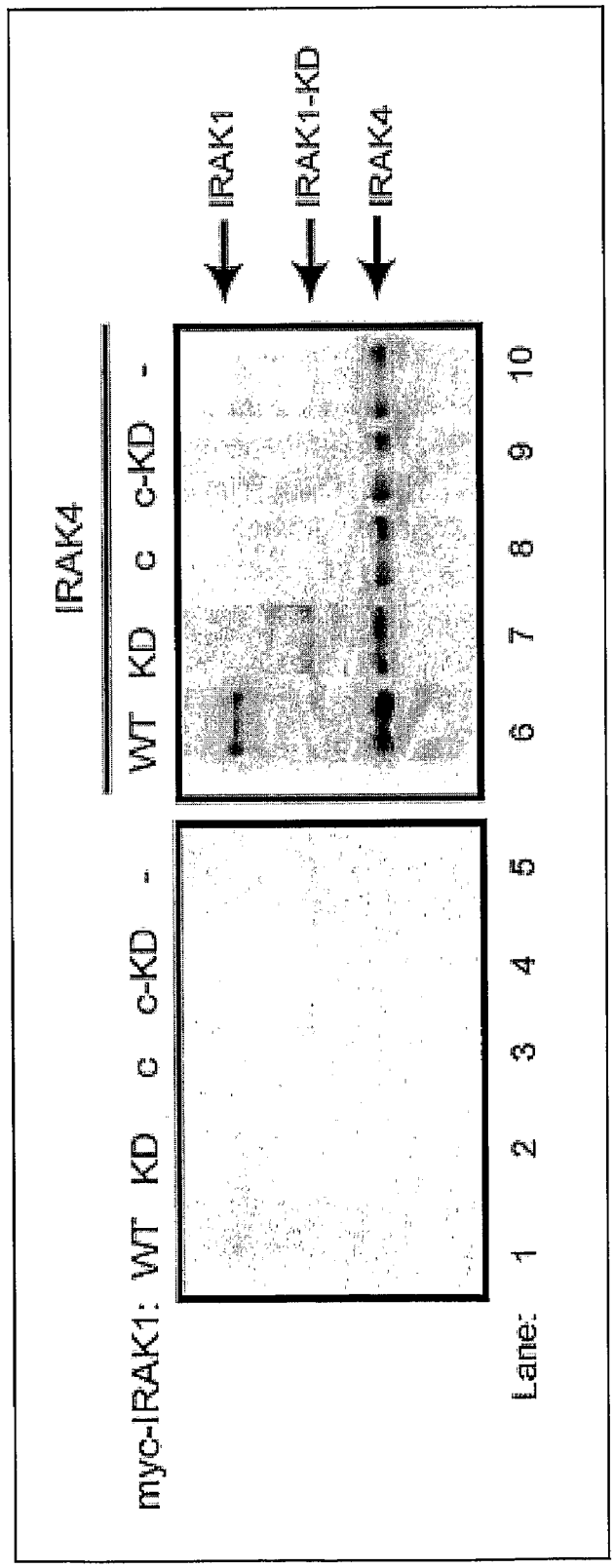
FIG. 8 demonstrates that IRAK1c cannot be phosphorylated by IRAK4. 293T cells were transfected with the indicated IRAK1 constructs, and lysates prepared 48 hr post-transfection were immunoprecipitated with the anti-myc antibody. The immunoprecipitates were then subjected to in vitro kinase assays both in the presence and in the absence of recombinant IRAK4, as indicated.

Initial analyses indicated that IRAK1c has no kinase activity (FIG. 3). In light of the recent data concerning the sequential activation of IRAK1 (Kollewe et al., 2004, *Journal of Biological Chemistry* 279:5227-5236), IRAK4 was tested for the ability to mediate the initial IRAK1c phosphorylation events. 293T cells were transfected with 1 μg of the myc-IRAK expression vectors indicated in FIG. 8, lysed 48 hours post-transfection, and anti-myc immunoprecipitates from 1000 μg of lysate were prepared, as described above. The protein bound to protein G-Sepharose beads were split into two reactions and subjected to an in vitro kinase assay, as described above, in the absence or presence of recombinant IRAK4, (FIG. 8). As previously demonstrated (FIG. 3), myc-IRAK1 showed strong autophosphorylation, while like myc-IRAK1-KD, IPAK1c exhibited no kinase activity. However, when incubated with recombinant IRAK4, a phosphorylated band was detected that corresponded to IPAK1-KD.

Based upon the model proposed by Kollewe et al. (Kollewe et al., 2004, *Journal of Biological Chemistry* 279:5227-5236, it is believed that this phosphorylation that is IRAK4-dependent corresponds to phosphorylation on Thr$^{203}$ and/or Thr$^{387}$. However, since a point mutation renders this protein kinase dead, it is believed to be unable to mediate the autophosphorylation in the ProST region that results in IRAK1 hyperphosphorylation and the corresponding shift in molecular weight. Neither IPAK1c nor IPAK1c-KD showed any phosphorylation in the presence of IRAK4. Based upon this data, it is believed that the IRAK1c splice variant is not phosphorylated by IRAK4, and thus is unable to become fully activated.

EXAMPLE 8

Analysis of IRAK1c-Tollip Interaction Before and After TIR Activation

IRAK1 was next analyzed for the ability to interact with the Tollip protein before stimulation with IL-1β.

Figure 9:
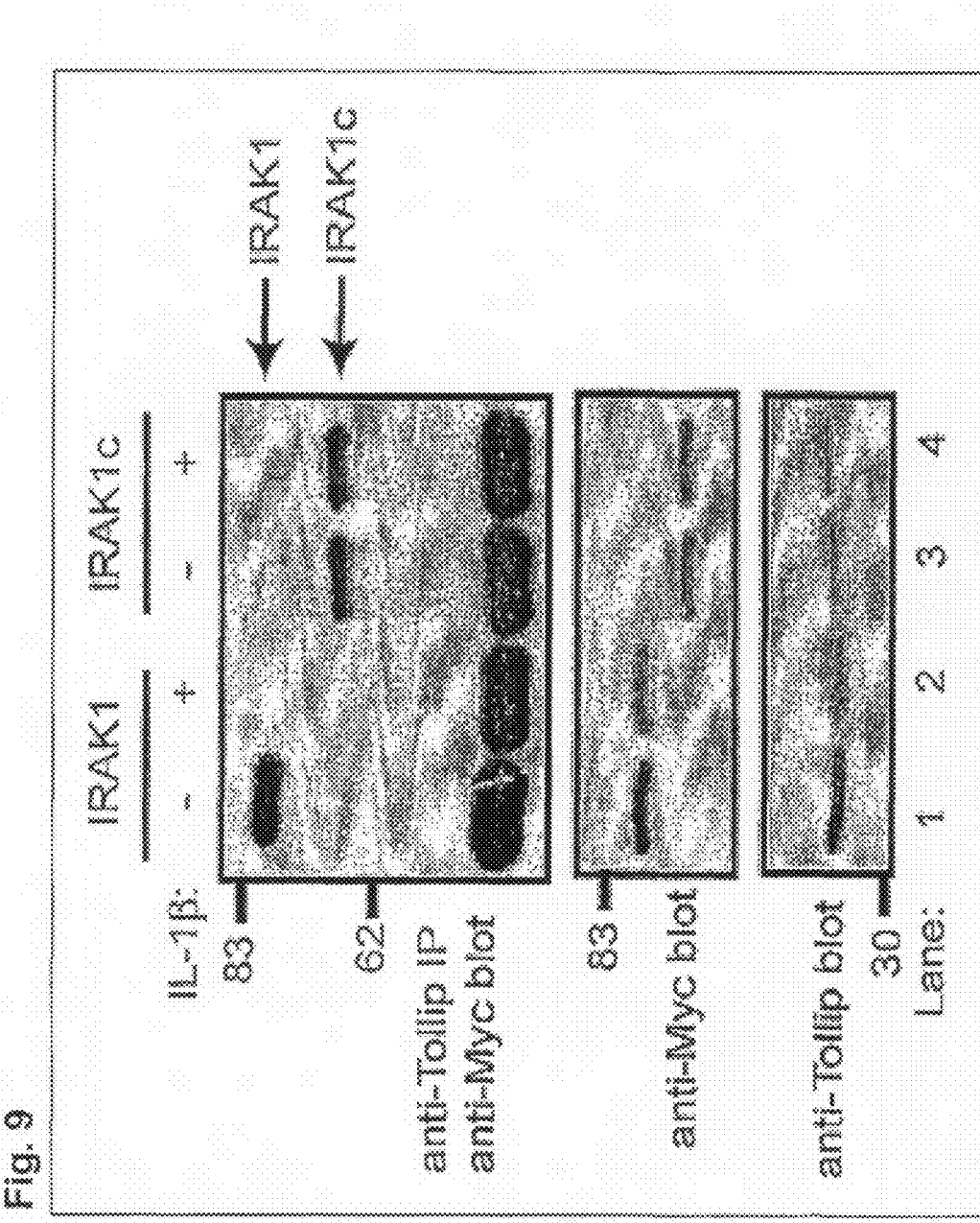
FIG. 9 shows that IRAK1c remains associated with Tollip after IL-1 receptor activation. G292 stable transfectants expressing myc-IRAK1 or myc-IRAK1c were stimulated with 5 ng/ml IL-1β for 3 min. or not stimulated ("+" or "−", respectively). Cell lysates were prepared and immunoprecipitated with anti-Tollip antibody/antiserum, followed by anti-myc immunoblotting. Whole cell lysates were also immunoblotted with anti-myc and anti-Tollip antibodies to confirm protein expression.

G292 cells were transfected with myc-IRAK1 and myc-IRAK1c expression vectors. Cells were either left unstimulated or stimulated with 5 ng/ml IL-1β for three minutes, followed bypreparation of lysates. Mouse monoclonal anti-Tollip antibody (Alexis) immunoprecipitates were separated by SDS-PAGE and immunoblotted with the anti-myc antibody to visualize associated IRAK1 or IRAK1c (FIG. 9). As previously reported (Kollewe et al., 2004, *Journal of Biological Chemistry* 279:5227-5236; Burns et al., 2000, *Nature Cell Biology* 2:346-351), IPAK1 was found to be associated with Tollip prior to activation (lane 1). Upon activation with IL-1β, IRAK1 became phosphorylated and exhibited kinase activity. IRAK1 also no longer associated with Tollip (FIG. 9, lane 2). However, the IRAK1c splice variant remained associated with Tollip after IL-1β stimulation (FIG. 9, lane 3). Similar results were obtained using THP-1 cells stimulated with LPS.

Based upon these results, it is believed that because IRAK1c cannot be phosphorylated by IRAK4 and lacks kinase activity, it cannot disengage from Tollip upon TIR activation, and thus fails to activate downstream signaling mediated by TRAF6.

EXAMPLE 9

Induction of IRAK1c Expression in Human Macrophages and Dendritic Cells

Figure 10:
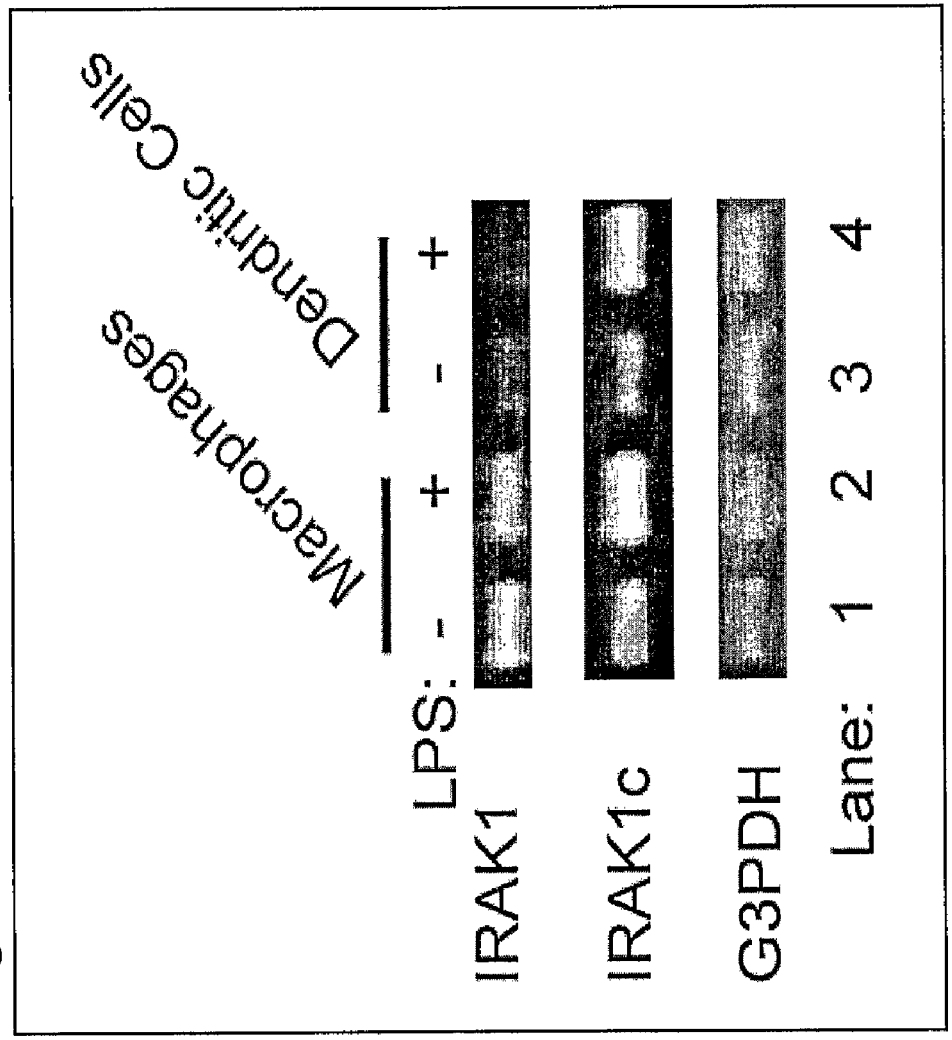
FIG. 10 demonstrates upregulation or IRAK1c in human dendritic cells and monocytes upon LPS treatment. Human dendritic cells and monocytes were prepared from whole blood and either unstimulated or stimulated with 100 ng/ml LPS for 6 hr. IRAK1 and IRAK1c mRNA were prepared, and cDNA was amplified via reverse transcriptase-PCR using IRAK1 and IRAK1c-specific primers. GAPDH amplification was used as a control.

To test whether IRAK1c expression is inducible, human monocytes and dendritic cells from peripheral human blood were prepared. Cells were then stimulated with 100 ng/ml LPS and cDNA was prepared for reverse transcriptase (RT) PCR analyses of IRAK1 versus IRAK1c expression (FIG. 10). Although dendritic cells expressed lower levels of IRAK1, IRAK1c expression was induced in both macrophages and dendritic cells upon LPS stimulation. As has been previously reported, a slight decrease in IRAK1 expression was observed upon LPS stimulation in macrophages (Yeo et al., 2003, *Journal of Immunology* 171:1052-1061).

These data reflect that, together with inducible regulators like IRAKM, the splice variant IRAK1c can function as a regulator to suppress or fine tune signaling downstream of TIRs.

EXAMPLE 10

IRAK1c Expression in Human Cancer Cell Lines

In order to assay the expression profiles of IRAK1 and IRAK1c in cancer cells, western analysis of several different human cancer cell lines was performed as described above.

Figure 11:
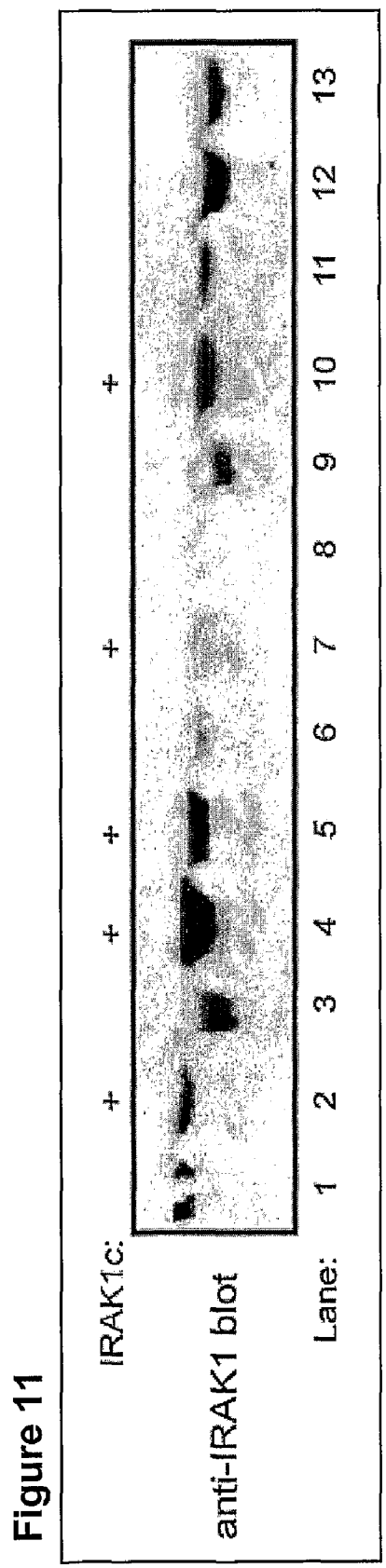
FIG. 11 illustrates western analysis of IRAK1 and IRAK1c expression in several different human cancer cell lines. The following cell lines were assayed: HRE (lane 1), A2058 (lane 2), HeLa (lane 3), SkMe12 (lane 4), A375 (lane 5), 293 (lane 6), SkMe131 (lane 7), WM266-4 (lane 8), DLD1 (lane 9), SkMe128 (lane 10), L5411N (lane 11), Ramos (lane 12), and E6.1 Jurkat (lane 13). Cells were lysed, and 100 μg of whole cell lysate was immunoblotted with anti-IRAK1 antibody. The presence of IRAK1c is reflected by the presence of faster-migrating, anti-IRAK1 antibody-reacting bands in lanes 2, 4, 5, 7, and 10.

The following cell lines were assayed as represented in FIG. 11: HRE (lane 1), A2058 (lane 2), HeLa (lane 3), SkMe12 (lane 4), A375 (lane 5), 293 (lane 6), SkMe13l (lane 7), WM266-4 (lane 8), DLD1 (lane 9), SkMe128 (lane 10), L5411N (lane 11), Ramos (lane 12), and E6.1 Jurkat (lane 13). Cells were lysed, and 100 µg of whole cell lysate was immunoblotted with anti-IRAK1 antibody. The presence of IRAK1c was reflected by the presence of faster migrating anti-IRAK1 antibody-reacting bands in lanes 2, 4, 5, 7, and 10).

EXAMPLE 11

Figure 12:
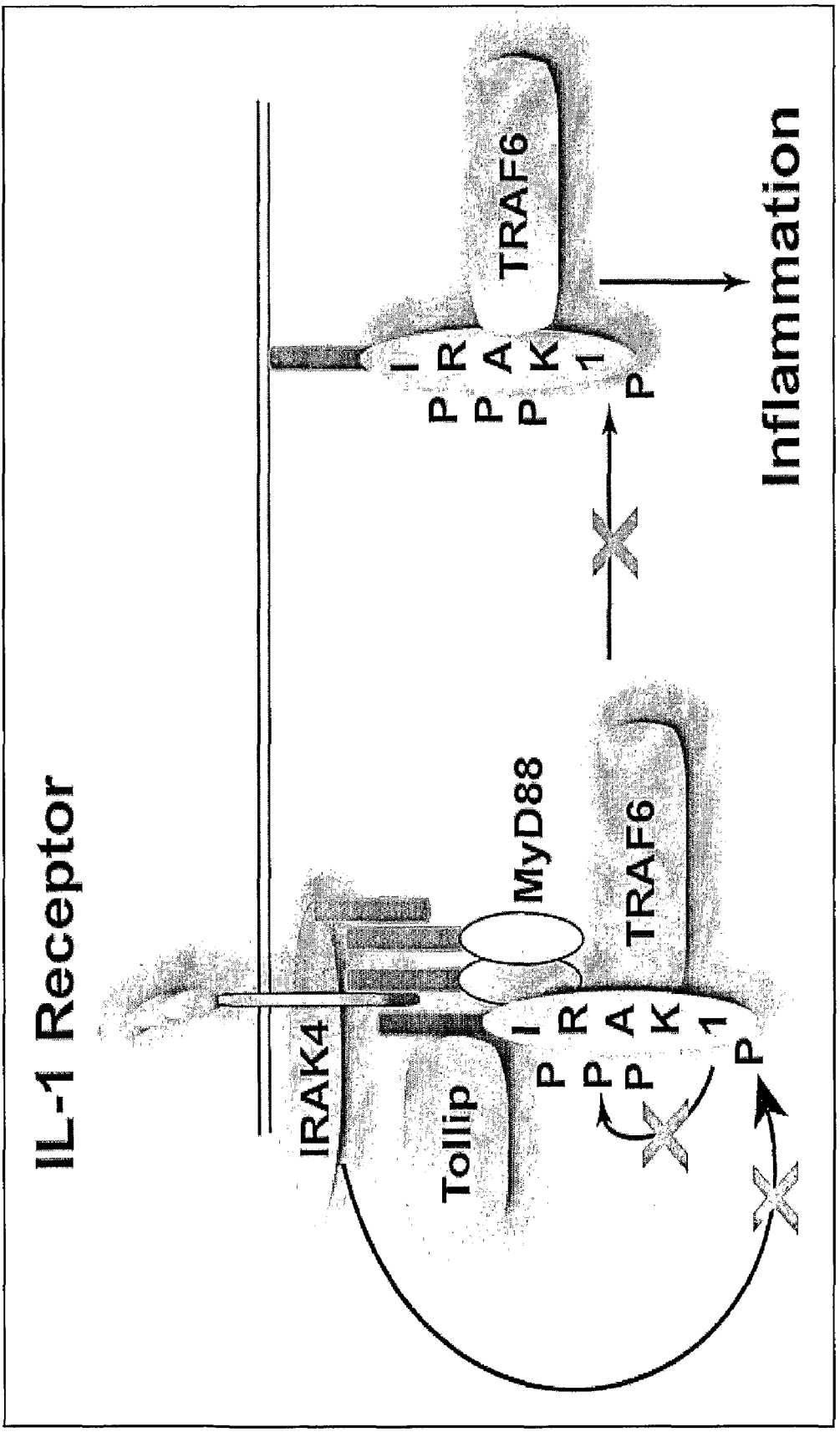
FIG. 12 illustrates a mechanistic model of IRAK1c regulation in TIR activity in vivo. Upon TIR activation by the appropriate ligand, Tollip-IRAK1 is recruited to the membrane and interacts with MyD88 and TRAF6. IRAK4 phosphorylates IRAK1 resulting in IRAK1 autophosphorylation and activation. IRAK1 then disengages from the receptor complex containing MyD88 and Tollip, and together with TRAF6, activates the NF-κB pathway, resulting in the production of proinflammatory cytokines. The splice variant IRAK1c cannot be phosphorylated by IRAK4, does not undergo autophosphorylation, and thus remains bound to the receptor (indicated by "X"s on arrows). As a result, IRAK1c does not disengage from the MyD88-Tollip-IRAK1c complex, and thus cannot form the requisite TRAF6-IRAK1 complex to effect activation of NF-κB.

Model for Mechanism of Action and Biological Function of the IRAK1c Splice Variant in TIR-Mediated Signaling Based on the results presented in the previous Examples, the splice variant IRAK1c appears to function, at least in part, as a natural dominant negative of full length IRAK1 activity, and therefore as a dominant negative inhibitor of TIP mediated signaling. At the molecular level, it is believed that the dominant negative phenotype function derives, at least in part, from the inability of IRAK4 to phosphorylate IRAK1c in response to TIR activation (e.g., via ligand binding). The inability to phosphorylate IRAK1c disallows for IRAK1c autophosphorylation, which in turn prevents disassociation of IRAK1c from Tollip at the receptor complex. This constitutive association with Tollip prevents formation of an IRAK1c-TRAF6 complex, disengagement of this complex from the receptor, and activation of downstream effector molecules such as NF-$_\kappa$B. Consequently, a functional role, of the IRAK1c splice variant is to attenuate key proinflammatory signaling pathways (FIG. 12).

Although the various aspects of the invention have been illustrated above by reference to examples and preferred embodiments, it will be appreciated that the scope of the invention is defined not by the foregoing detailed description, but by the following claims as properly construed under principles of patent law.

What is claimed is:

1. An isolated polynucleotide having the nucleic acid sequence set forth in SEQ ID NO:7.

2. An isolated polynucleotide as defined in claim 1 in substantially pure form.

3. An isolated and purified biologically active polypeptide having the amino acid sequence set forth in SEQ ID NO:9.

4. An isolated and purified biologically active polypeptide as defined in claim 3 having a purity of at least 99%.

5. An expression vector comprising the polynucleotide having the nucleic acid sequence set forth in SEQ ID NO:7 operably linked to a promoter element that expresses the polypeptide encoded by said polynucleotide in a transfected host cell.

6. An isolated recombinant host cell that has been transfected or transformed by an expression vector as defined in claim 5, wherein said host cell expresses the polypeptide.

* * * * *